(12) United States Patent
Ostedgaard et al.

(10) Patent No.: US 7,407,801 B2
(45) Date of Patent: Aug. 5, 2008

(54) TRUNCATED CMV PROMOTERS AND VECTORS CONTAINING SAME

(75) Inventors: Lynda S. Ostedgaard, Iowa City, IA (US); Michael J. Welsh, Riverside, IA (US); Mark F. Stinski, North Liberty, IA (US); John A. Chiorini, Kensington, MD (US)

(73) Assignees: University of Iowa Research Foundation, Iowa City, IA (US); National Institutes of Health (NIH), Bethesda, MD (US)

( * ) Notice: Subject to any disclaimer, the term of this patent is extended or adjusted under 35 U.S.C. 154(b) by 0 days.

(21) Appl. No.: 11/005,410

(22) Filed: Dec. 6, 2004

(65) Prior Publication Data

US 2007/0098690 A1 May 3, 2007

Related U.S. Application Data

(60) Provisional application No. 60/527,146, filed on Dec. 5, 2003.

(51) Int. Cl.
| | |
|---|---|
| C12N 15/70 | (2006.01) |
| C12N 15/74 | (2006.01) |
| C12N 15/85 | (2006.01) |
| C12N 15/86 | (2006.01) |
| C12N 15/864 | (2006.01) |
| A61K 48/00 | (2006.01) |

(52) U.S. Cl. .................. 435/320.1; 435/325; 435/456; 536/24.1; 424/93.2; 514/44

(58) Field of Classification Search .................. None
See application file for complete search history.

(56) References Cited

U.S. PATENT DOCUMENTS

| | | | |
|---|---|---|---|
| 5,168,062 | A | 12/1992 | Stinski |
| 5,385,839 | A | 1/1995 | Stinski |
| 5,849,522 | A | 12/1998 | Fleckenstein et al. |
| 5,872,005 | A | 2/1999 | Wang et al. |
| 6,218,140 | B1 | 4/2001 | Fleckenstein et al. |
| 2004/0038402 | A1* | 2/2004 | Antoniou et al. ............ 435/455 |

FOREIGN PATENT DOCUMENTS

WO  WO 2003014298 A2 *  2/2003

OTHER PUBLICATIONS

Orkin et al., Report and Recommendations of the Panel to Assess the NIH Investment in Research on Gene Therapy, issued by the U.S. National Institutes of Health, Dec. 7, 1995.*

Driskell et al., "Current status of gene therapy for inherited lung diseases," Annu. Rev. Physiol. 65: 585-612, 2003.*

Isomura H, Tsurumi T, Stinski MF. "Role of the proximal enhancer of the major immediate-early promoter in human cytomegalovirus replication," J Virol. Dec. 2004;78(23):12788-99.

Isomura H, Stinski MF. "The human cytomegalovirus major immediate-early enhancer determines the efficiency of immediate-early gene transcription and viral replication in permissive cells at low multiplicity of infection," J Virol. Mar. 2003;77(6):3602-14.

Meier JL, Keller MJ, McCoy JJ. "Requirement of multiple cis-acting elements in the human cytomegalovirus major immediate-early distal enhancer for viral gene expression and replication," J Virol. Jan. 2002;76(1):313-26.

Ostedgaard LS, Zabner J, Vermeer DW, Tokhlina T, Karp PH, Stecenko AA, Randak C, and Welsh MJ. CFTR With a Partially Deleted R Domain Corrects the Cystic Fibrosis Chloride Transport Defect in Human Airway Epithelia In Vitro and in Mouse Nasal Mucosa In Vivo . Proc. Natl. Acad. Sci. USA, 99: 3093-3098, 2002.

Davies et al., 2001, "Gene therapy for cystic fibrosis," J. Gene Med. 3:409-417.

Ostegaard et al., 2001, "Regulation of the cystic fibrosis transmembrane conductance regulator CI-channel by its R domain," J. Biol. Chem. 276:7689-92.

Csanady et al., 2000, "Severed channels probe regulation of gating of cystic fibrosis transmembrane conductance regulator by its cytoplasmic domains," J. Gen. Physiol. 116:477-500.

Meier JL, Pruessner JA. "The human cytomegalovirus major immediate-early distal enhancer region is required for efficient viral replication and immediate-early gene expression," J Virol. Feb. 2000;74(4):1602-13.

Ostedgaard, et al., 2000, "A functional R domain from cystic fibrosis transmembrane conductance regulator is predominantly unstructured in solution," Proc. Natl. Acad. Sci. U.S.A. 97:5657-62.

Zabner et al., 2000, "Adeno-associated virus type 5 (AAV5) but not AAV2 binds to the apical surfaces of airway epithelia and facilitates gene transfer," J. Virol. 74:3852-8.

Rabinowitz et al., 2000, "Building a better vector: the manipulation of AAV virions," Virology 278:301-308.

Xie et al., 2000, "Conformation, independent of charge, in the R domain affects cystic fibrosis transmembrane conductance regulator channel openings," Biophys. J. 78:1293-1305.

Chiorini et al., 1999, "Cloning and characterization of adeno-associated virus type 5," J. Virol. 73:1309-1319.

(Continued)

Primary Examiner—Scott D Priebe
(74) Attorney, Agent, or Firm—McKee, Voorhees & Sease, P.L.C.

(57) ABSTRACT

The present invention relates to nucleic acid molecules comprising certain truncated forms of the human cytomegalovirus (CMV) immediate-early enhancer-promoter, either alone or operably linked to transgenes of interest, including those encoding partially-deleted CFTR proteins. This invention further relates to vectors comprising these nucleic acid molecules and host cells transformed by such vectors. The nucleic acid molecules, vectors and transformed host cells of the present invention are useful for treating a variety of genetic, metabolic and acquired diseases, including inter alia cystic fibrosis (CF) airway disease.

16 Claims, 13 Drawing Sheets

OTHER PUBLICATIONS

Wang et al., 1999, "Efficient CFTR expression from AAV vectors packaged with promoters—the second generation," Gene Therapy 6:667-675.

Flotte, 1999, "Gene therapy for cystic fibrosis," Curr. Opin Mol. Ther. 1:510-516.

Welsh, 1999, "Gene transfer for cystic fibrosis," J. Clin. Invest. 104:1165-1166.

Hernandez et al., "Latent adeno-associated virus infection elicits humoral but not cell-mediated immune responses in a nonhuman primate model," 1999, J. Virol. 73:8549-8558.

Stinski, 1999, Cytomegalovirus promoter for expression in mammalian cells. In Gene Expression Systems: Using Nature for the Art of Expression. Academic Press, New York. pp. 211-233.

Vankeerberghen et al., 1999, "Functional characterization of the CFTR R domain using CFTR/MDR1 hybrid and delection constructs," Biochemistry 38:14988-998.

Zhang et al., 1998, "Efficient expression of CFTR function with adeno-associated virus vectors that carry shortened CFTR genes," Proc. Natl. Acad. Sci. USA 95:10158-163.

Ma et al., 1997, "Function of the R domain in the cystic fibrosis transmembrane conductance regulator chloride channel," J. Biol. Chem. 272:28133-34.

Yew et al., 1997, "Optimization of plasmid vectors for high-level expression in lung epithelial cells," Human Gene Therapy 8:575-84.

Dong et al., 1996, "Quantitative analysis of the packaging capacity of recombinant adeno-associated virus," Human Gene Therapy 7: 2101-12.

Jiang et al., 1996, "Ability of adenovirus vectors containing different CFTR transcriptional cassettes to correct ion transport defects in CF cells," Am. J. Physiol. 271:L527-37.

Phelps et al., 1995, "Expression of full-length and truncated dystrophin mini-genes in transgenic mdx mice," Hum. Mol. Genet. 4:1251-8.

Welsh MJ, Tsui L-C, Boat TF, Beaudet AL. Cystic fibrosis. In: Scriver CR, Beaudet AL, Sly WS, Valle D, editors. The metabolic and molecular basis of inherited diseases. 7th ed. New York: McGraw-Hill, 1995:3799-876.

Flotte et al., 1993, "Expression of the cystic fibrosis transmembrane conductance regulator from a novel adeno-associated virus promoter," J. Biol. Chem. 268:3781-3790.

Rich et al., 1993, "Effect of deletion mutations on the functions of CFTR chloride channels,"Receptors Channels 1:221-232.

Rich et al., 1991, "Effect of deleting the R domain on CFTR-generated chloride channels," Science 253:205-7.

Levitt et al., 1989, "Definition of an efficient synthetic poly(A) site," Genes Dev. 3:1019-25.

Riordan et al., 1989, "Identification of the cystic fibrosis gene: cloning and characterization of complementary DNA," Science 245:1066-73.

Stinski and Roehr, 1985, "Activation of the major immediate early gene of human cytomegalovirus by cis-acting elements in the promoter-regulatory sequence and by virus-specific trans-acting components," J. Virol. 55:431-41.

* cited by examiner

Fig. 3

(SEQ ID NO. 4)

CMV173-CFTRΔR

`GCGGCCGC`ACTCACGGGGATTTCCAAGTCTCCACCCCATTGACGTCAATGGGAGTTTGT
TTTGGCACCAAAATCAACGGGACTTTCCAAAATGTCGTAATAACCCCGCCCCGTTGACG
CAAATGGGCGGTAGGCGTGTACGGTGGGAGGTCTATATAAGCAGAGCTCGTTTAGTGAA
CCGTCAGAATTCTCGAGTGATCGAAAGAGCCTGCTAAAGCAAAAAAGAAGTCACCATGC
AGAGGTCGCCTCTGGAAAAGGCCAGCGTTGTCTCCAAACTTTTTTTCAGCTGGACCAGA
CCAATTTTGAGGAAAGGATACAGACAGCGCCTGGAATTGTCAGACATATACCAAATCCC
TTCTGTTGATTCTGCTGACAATCTATCTGAAAAATTGGAAAGAGAATGGGATAGAGAGC
TGGCTTCAAAGAAAAATCCTAAACTCATTAATGCCCTTCGGCGATGTTTTTCTGGAGA
TTTATGTTCTATGGAATCTTTTTATATTTAGGGGAAGTCACCAAAGCAGTACAGCCTCT
CTTACTGGGAAGAATCATAGCTTCCTATGACCCGGATAACAAGGAGGAACGCTCTATCG
CGATTTATCTAGGCATAGGCTTATGCCTTCTCTTTATTGTGAGGACACTGCTCCTACAC
CCAGCCATTTTTGGCCTTCATCACATTGGAATGCAGATGAGAATAGCTATGTTTAGTTT
GATTTATAAGAAGACTTTAAAGCTGTCAAGCCGTGTTCTAGATAAAATAAGTATTGGAC
AACTTGTTAGTCTCCTTTCCAACAACCTGAACAAATTTGATGAAGGACTTGCATTGGCA
CATTTCGTGTGGATCGCTCCTTTGCAAGTGGCACTCCTCATGGGGCTAATCTGGGAGTT
GTTACAGGCGTCTGCCTTCTGTGGACTTGGTTTCCTGATAGTCCTTGCCCTTTTTCAGG
CTGGGCTAGGGAGAATGATGATGAAGTACAGAGATCAGAGAGCTGGGAAGATCAGTGAA
AGACTTGTGATTACCTCAGAAATGATTGAAAATATCCAATCTGTTAAGGCATACTGCTG
GGAAGAAGCAATGGAAAAATGATTGAAAACTTAAGACAAACAGAACTGAAACTGACTC
GGAAGGCAGCCTATGTGAGATACTTCAATAGCTCAGCCTTCTTCTTCTCAGGGTTCTTT
GTGGTGTTTTATCTGTGCTTCCCTATGCACTAATCAAAGGAATCATCCTCCGGAAAAT
ATTCACCACCATCTCATTCTGCATTGTTCTGCGCATGGCGGTCACTCGGCAATTTCCCT
GGGCTGTACAAACATGGTATGACTCTCTTGGAGCAATAAACAAAATACAGGATTTCTTA
CAAAAGCAAGAATATAAGACATTGGAATATAACTTAACGACTACAGAAGTAGTGATGGA
GAATGTAACAGCCTTCTGGGAGGAGGGATTTGGGGAATTATTTGAGAAAGCAAAACAAA
ACAATAACAATAGAAAAACTTCTAATGGTGATGACAGCCTCTTCTTCAGTAATTTCTCA
CTTCTTGGTACTCCTGTCCTGAAAGATATTAATTTCAAGATAGAAAGAGGACAGTTGTT
GGCGGTTGCTGGATCCACTGGAGCAGGCAAGACTTCACTTCTAATGATGATTATGGGAG
AACTGGAGCCTTCAGAGGGTAAAATTAAGCACAGTGGAAGAATTTCATTCTGTTCTCAG
TTTTCCTGGATTATGCCTGGCACCATTAAAGAAAATATCATCTTTGGTGTTTCCTATGA
TGAATATAGATACAGAAGCGTCATCAAAGCATGCCAACTAGAAGAGGACATCTCCAAGT
TTGCAGAGAAAGACAATATAGTTCTTGGAGAAGGTGGAATCACACTGAGTGGAGGTCAA
CGAGCAAGAATTTCTTTAGCAAGAGCAGTATACAAAGATGCTGATTTGTATTTATTAGA
CTCTCCTTTTGGATACCTAGATGTTTTAACAGAAAAGAAATATTTGAAAGCTGTGTCT
GTAAACTGATGGCTAACAAAACTAGGATTTGGTCACTTCTAAAATGGAACATTTAAAG
AAAGCTGACAAAATATTAATTTTGCATGAAGGTAGCAGCTATTTTATGGGACATTTTC
AGAACTCCAAAATCTACAGCCAGACTTTAGCTCAAAACTCATGGGATGTGATTCTTTCG
ACCAATTTAGTGCAGAAGAAGAAATTCAATCCTAACTGAGACCTTACACCGTTTCTCA
TTAGAAGGAGATGCTCCTGTCTCCTGGACAGAAACAAAAAAACAATCTTTTAAACAGAC

Fig. 3 (continued)

```
TGGAGAGTTTGGGGAAAAAAGGAAGAATTCTATTCTCAATCCAATCAACTCT***ACGC
TTCAGGCACGAAGGAGGCAGTCTGTCCTGAACCTGATGACACACTCAGTTAACCAAGGT
CAGAACATTCACCGAAAGACAACAGCATCCACACGAAAGTGTCACTGGCCCCTCAGGC
AAACTTGACTGAACTGGATATATATTCAAGAAGGTTATCTCAAGAAACTGGCTTGGAAA
TAAGTGAAGAAATTAACGAAGAAGACTTAAAGGAGTGCTTTTTTGATGATATGGAGAGC
ATACCAGCAGTGACTACATGGAACACATACCTTCGATATATTACTGTCCACAAGAGCTT
AATTTTTGTGCTAATTTGGTGCTTAGTAATTTTTCTGGCAGAGGTGGCTGCTTCTTTGG
TTGTGCTGTGGCTCCTTGGAAACACTCCTCTTCAAGACAAAGGGAATAGTACTCATAGT
AGAAATAACAGCTATGCAGTGATTATCACCAGCACCAGTTCGTATTATGTGTTTTACAT
TTACGTGGGAGTAGCCGACACTTTGCTTGCTATGGATTCTTCAGAGGTCTACCACTGG
TGCATACTCTAATCACAGTGTCGAAAATTTTACACCACAAAATGTTACATTCTGTTCTT
CAAGCACCTATGTCAACCCTCAACACGTTGAAAGCAGGTGGGATTCTTAATAGATTCTC
CAAAGATATAGCAATTTTGGATGACCTTCTGCCTCTTACCATATTTGACTTCATCCAGT
TGTTATTAATTGTGATTGGAGCTATAGCAGTTGTCGCAGTTTTACAACCCTACATCTTT
GTTGCAACAGTGCCAGTGATAGTGGCTTTTATTATGTTGAGAGCATATTTCCTCCAAAC
CTCACAGCAACTCAAACAACTGGAATCTGAAGGCAGGAGTCCAATTTTCACTCATCTTG
TTACAAGCTTAAAAGGACTATGGACACTTCGTGCCTTCGGACGGCAGCCTTACTTTGAA
ACTCTGTTCCACAAAGCTCTGAATTTACATACTGCCAACTGGTTCTTGTACCTGTCAAC
ACTGCGCTGGTTCCAAATGAGAATAGAAATGATTTTTGTCATCTTCTTCATTGCTGTTA
CCTTCATTTCCATTTTAACAACAGGAGAAGGAGAAGGAAGAGTTGGTATTATCCTGACT
TTAGCCATGAATATCATGAGTACATTGCAGTGGGCTGTAAACTCCAGCATAGATGTGGA
TAGCTTGATGCGATCTGTGAGCCGAGTCTTTAAGTTCATTGACATGCCAACAGAAGGTA
AACCTACCAAGTCAACCAAACCATACAAGAATGGCCAACTCTCGAAAGTTATGATTATT
GAGAATTCACACGTGAAGAAAGATGACATCTGGCCCTCAGGGGGCCAAATGACTGTCAA
AGATCTCACAGCAAAATACACAGAAGGTGGAAATGCCATATTAGAGAACATTTCCTTCT
CAATAAGTCCTGGCCAGAGGGTGGGCCTCTTGGGAAGAACTGGATCAGGGAAGAGTACT
TTGTTATCAGCTTTTTTGAGACTACTGAACACTGAAGGAGAAATCCAGATCGATGGTGT
GTCTTGGGATTCAATAACTTTGCAACAGTGGAGGAAAGCCTTTGGAGTGATACCACAGA
AAGTATTTATTTTTCTGGAACATTTAGAAAAACTTGGATCCCTATGAACAGTGGAGT
GATCAAGAAATATGGAAAGTTGCAGATGAGGTTGGGCTCAGATCTGTGATAGAACAGTT
TCCTGGGAAGCTTGACTTTGTCCTTGTGGATGGGGCTGTGTCCTAAGCCATGGCCACA
AGCAGTTGATGTGCTTGGCTAGATCTGTTCTCAGTAAGGCGAAGATCTTGCTGCTTGAT
GAACCCAGTGCTCATTTGGATCCAGTAACATACCAAATAATTAGAAGAACTCTAAAACA
AGCATTTGCTGATTGCACAGTAATTCTCTGTGAACACAGGATAGAAGCAATGCTGGAAT
GCCAACAATTTTTGGTCATAGAAGAGAACAAAGTGCGGCAGTACGATTCCATCCAGAAA
CTGCTGAACGAGAGGAGCCTCTTCCGGCAAGCCATCAGCCCTCCGACAGGGTGAAGCT
CTTTCCCCACCGGAACTCAAGCAAGTGCAAGTCTAAGCCCCAGATTGCTGCTCTGAAAG
AGGAGACAGAAGAAGAGGTGCAAGATACAAGGCTTTAGAATAAAACATCTTTATTTTCA
TTACATCTGTGTGTTGGTTTTTTGTGTGGCGGCCGC
```

Fig. 4

(SEQ ID NO. 5)

113CMV-CFTRΔR

GCGGCCGCAAAATCAACGGGACTTTCCAAAATGTCGTAATAACCCCGCCCCGTTGACGC
AAATGGGCGGTAGGCGTGTACGGTGGGAGGTCTATATAAGCAGAGCTCGTTTAGTGAAC
CGTCAGAATTCTCGAGTGATCGAAAGAGCCTGCTAAAGCAAAAAAGAAGTCACCATGCA
GAGGTCGCCTCTGGAAAAGGCCAGCGTTGTCTCCAAACTTTTTTTCAGCTGGACCAGAC
CAATTTTGAGGAAAGGATACAGACAGCGCCTGGAATTGTCAGACATATACCAAATCCCT
TCTGTTGATTCTGCTGACAATCTATCTGAAAAATTGGAAAGAGAATGGGATAGAGAGCT
GGCTTCAAAGAAAAATCCTAAACTCATTAATGCCCTTCGGCGATGTTTTTCTGGAGAT
TTATGTTCTATGGAATCTTTTTATATTTAGGGGAAGTCACCAAAGCAGTACAGCCTCTC
TTACTGGGAAGAATCATAGCTTCCTATGACCCGGATAACAAGGAGGAACGCTCTATCGC
GATTTATCTAGGCATAGGCTTATGCCTTCTCTTTATTGTGAGGACACTGCTCCTACACC
CAGCCATTTTTGGCCTTCATCACATTGGAATGCAGATGAGAATAGCTATGTTTAGTTTG
ATTTATAAGAAGACTTTAAAGCTGTCAAGCCGTGTTCTAGATAAAATAAGTATTGGACA
ACTTGTTAGTCTCCTTTCCAACAACCTGAACAAATTTGATGAAGGACTTGCATTGGCAC
ATTTCGTGTGGATCGCTCCTTTGCAAGTGGCACTCCTCATGGGGCTAATCTGGGAGTTG
TTACAGGCGTCTGCCTTCTGTGGACTTGGTTTCCTGATAGTCCTTGCCCTTTTTCAGGC
TGGGCTAGGGAGAATGATGATGAAGTACAGAGATCAGAGAGCTGGGAAGATCAGTGAAA
GACTTGTGATTACCTCAGAAATGATTGAAAATATCCAATCTGTTAAGGCATACTGCTGG
GAAGAAGCAATGGAAAAATGATTGAAAACTTAAGACAAACAGAACTGAAACTGACTCG
GAAGGCAGCCTATGTGAGATACTTCAATAGCTCAGCCTTCTTCTTCTCAGGGTTCTTTG
TGGTGTTTTTATCTGTGCTTCCCTATGCACTAATCAAAGGAATCATCCTCCGGAAAATA
TTCACCACCATCTCATTCTGCATTGTTCTGCGCATGGCGGTCACTCGGCAATTTCCCTG
GGCTGTACAAACATGGTATGACTCTCTTGGAGCAATAAACAAAATACAGGATTTCTTAC
AAAAGCAAGAATATAAGACATTGGAATATAACTTAACGACTACAGAAGTAGTGATGGAG
AATGTAACAGCCTTCTGGGAGGAGGGATTTGGGGAATTATTTGAGAAAGCAAAACAAAA
CAATAACAATAGAAAAACTTCTAATGGTGATGACAGCCTCTTCTTCAGTAATTTCTCAC
TTCTTGGTACTCCTGTCCTGAAAGATATTAATTTCAAGATAGAAAGAGGACAGTTGTTG
GCGGTTGCTGGATCCACTGGAGCAGGCAAGACTTCACTTCTAATGATGATTATGGGAGA
ACTGGAGCCTTCAGAGGGTAAAATTAAGCACAGTGGAAGAATTTCATTCTGTTCTCAGT
TTTCCTGGATTATGCCTGGCACCATTAAAGAAAATATCATCTTTGGTGTTTCCTATGAT
GAATATAGATACAGAAGCGTCATCAAAGCATGCCAACTAGAAGAGGACATCTCCAAGTT
TGCAGAGAAAGACAATATAGTTCTTGGAGAAGGTGGAATCACACTGAGTGGAGGTCAAC
GAGCAAGAATTTCTTTAGCAAGAGCAGTATACAAAGATGCTGATTTGTATTTATTAGAC
TCTCCTTTTGGATACCTAGATGTTTTAACAGAAAAGAAATATTTGAAAGCTGTGTCTG
TAAACTGATGGCTAACAAAACTAGGATTTTGGTCACTTCTAAAATGGAACATTTAAAGA
AAGCTGACAAAATATTAATTTTGCATGAAGGTAGCAGCTATTTTTATGGACATTTTCA
GAACTCCAAAATCTACAGCCAGACTTTAGCTCAAAACTCATGGGATGTGATTCTTTCGA
CCAATTTAGTGCAGAAGAAGAAATTCAATCCTAACTGAGACCTTACACCGTTTCTCAT
TAGAAGGAGATGCTCCTGTCTCCTGGACAGAAACAAAAAAACAATCTTTTAAACAGACT
GGAGAGTTTGGGGAAAAAAGGAAGAATTCTATTCTCAATCCAATCAACTCT***ACGCT
TCAGGCACGAAGGAGGCAGTCTGTCCTGAACCTGATGACACACTCAGTTAACCAAGGTC
AGAACATTCACCGAAAGACAACAGCATCCACACGAAAAGTGTCACTGGCCCCTCAGGCA

Fig. 4 (continued)

```
AACTTGACTGAACTGGATATATATTCAAGAAGGTTATCTCAAGAAACTGGCTTGGAAAT
AAGTGAAGAAATTAACGAAGAAGACTTAAAGGAGTGCTTTTTTGATGATATGGAGAGCA
TACCAGCAGTGACTACATGGAACACATACCTTCGATATATTACTGTCCACAAGAGCTTA
ATTTTTGTGCTAATTTGGTGCTTAGTAATTTTTCTGGCAGAGGTGGCTGCTTCTTTGGT
TGTGCTGTGGCTCCTTGGAAACACTCCTCTTCAAGACAAAGGGAATAGTACTCATAGTA
GAAATAACAGCTATGCAGTGATTATCACCAGCACCAGTTCGTATTATGTGTTTTACATT
TACGTGGGAGTAGCCGACACTTTGCTTGCTATGGATTCTTCAGAGGTCTACCACTGGT
GCATACTCTAATCACAGTGTCGAAAATTTTACACCACAAAATGTTACATTCTGTTCTTC
AAGCACCTATGTCAACCCTCAACACGTTGAAAGCAGGTGGGATTCTTAATAGATTCTCC
AAAGATATAGCAATTTTGGATGACCTTCTGCCTCTTACCATATTTGACTTCATCCAGTT
GTTATTAATTGTGATTGGAGCTATAGCAGTTGTCGCAGTTTTACAACCCTACATCTTTG
TTGCAACAGTGCCAGTGATAGTGGCTTTTATTATGTTGAGAGCATATTTCCTCCAAACC
TCACAGCAACTCAAACAACTGGAATCTGAAGGCAGGAGTCCAATTTTCACTCATCTTGT
TACAAGCTTAAAAGGACTATGGACACTTCGTGCCTTCGGACGGCAGCCTTACTTTGAAA
CTCTGTTCCACAAAGCTCTGAATTTACATACTGCCAACTGGTTCTTGTACCTGTCAACA
CTGCGCTGGTTCCAAATGAGAATAGAAATGATTTTTGTCATCTTCTTCATTGCTGTTAC
CTTCATTTCCATTTTAACAACAGGAGAAGGAGAAGGAAGAGTTGGTATTATCCTGACTT
TAGCCATGAATATCATGAGTACATTGCAGTGGGCTGTAAACTCCAGCATAGATGTGGAT
AGCTTGATGCGATCTGTGAGCCGAGTCTTTAAGTTCATTGACATGCCAACAGAAGGTAA
ACCTACCAAGTCAACCAAACCATACAAGAATGGCCAACTCTCGAAAGTTATGATTATTG
AGAATTCACACGTGAAGAAAGATGACATCTGGCCCTCAGGGGGCCAAATGACTGTCAAA
GATCTCACAGCAAAATACACAGAAGGTGGAAATGCCATATTAGAGAACATTTCCTTCTC
AATAAGTCCTGGCCAGAGGGTGGGCCTCTTGGGAAGAACTGGATCAGGGAAGAGTACTT
TGTTATCAGCTTTTTTGAGACTACTGAACACTGAAGGAGAAATCCAGATCGATGGTGTG
TCTTGGGATTCAATAACTTTGCAACAGTGGAGGAAAGCCTTTGGAGTGATACCACAGAA
AGTATTTATTTTTTCTGGAACATTTAGAAAAACTTGGATCCCTATGAACAGTGGAGTG
ATCAAGAAATATGGAAAGTTGCAGATGAGGTTGGGCTCAGATCTGTGATAGAACAGTTT
CCTGGGAAGCTTGACTTTGTCCTTGTGGATGGGGCTGTGTCCTAAGCCATGGCCACAA
GCAGTTGATGTGCTTGGCTAGATCTGTTCTCAGTAAGGCGAAGATCTTGCTGCTTGATG
AACCCAGTGCTCATTTGGATCCAGTAACATACCAAATAATTAGAAGAACTCTAAAACAA
GCATTTGCTGATTGCACAGTAATTCTCTGTGAACACAGGATAGAAGCAATGCTGGAATG
CCAACAATTTTTGGTCATAGAAGAGAACAAAGTGCGGCAGTACGATTCCATCCAGAAAC
TGCTGAACGAGAGGAGCCTCTTCCGGCAAGCCATCAGCCCCTCCGACAGGGTGAAGCTC
TTTCCCCACCGGAACTCAAGCAAGTGCAAGTCTAAGCCCCAGATTGCTGCTCTGAAAGA
GGAGACAGAAGAAGAGGTGCAAGATACAAGGCTTTAGAATAAAACATCTTTATTTTCAT
TACATCTGTGTGTTGGTTTTTTGTGTGGCGGCCGC
```

TRUNCATED CMV PROMOTERS AND VECTORS CONTAINING SAME

RELATED APPLICATIONS

The present application claims the benefit of U.S. Application No. 60/527,146 filed Dec. 5, 2003 which is incorporated herein by reference in its entirety. This disclosure contains information related to research performed with government support under grant HL61234 awarded by the National Institutes of Health. The government may have certain rights herein.

FIELD OF THE INVENTION

This invention relates to nucleic acid molecules comprising certain truncated forms of the human cytomegalovirus (CMV) immediate-early promoter, either alone or operably linked to transgenes of interest, including those encoding partially-deleted CFTR proteins. This invention further relates to vectors comprising these nucleic acid molecules and host cells transformed by these vectors. The nucleic acid molecules, vectors and transformed host cells of the present invention are useful for the treatment of a variety of genetic, metabolic and acquired diseases, including inter alia cystic fibrosis (CF) airway disease.

BACKGROUND OF THE INVENTION

Airway disease is the major cause of morbidity and mortality in cystic fibrosis (CF), an autosomal recessive disease caused by mutations in the gene encoding the cystic fibrosis transmembrane conductance regulator (CFTR) Cl$^-$ channel. Welsh et al., *The Metabolic and Molecular Basis of Inherited Disease*, eds. Scriver CR, Beaudet AL, Sly WS, Valle D, Childs B, Vogelstein B, McGraw-Hill, New York, 1995. Gene transfer offers the potential for a new and effective treatment for CF airway disease. For reviews see Davies et al., 2001, *J. Gene Med.* 3:409-417; Flotte, 1999, *Curr. Opin Mol. Ther.* 1:510-516; and Welsh, 1999, *J. Clin. Invest.* 104:1165-1166. Previous studies have shown the feasibility of transferring the CFTR cDNA to CF airway epithelial cells in vitro and in vivo. However, with most vectors, two main problems limit gene transfer: gene transfer across the apical surface of differentiated airway epithelia is inefficient, and expression of the transferred gene is transient. See Davies et al., 2001, *J. Gene Med.* 3:409-417; Flotte, 1999, *Curr. Opin Mol. Ther.* 1:510-516; and Welsh, 1999, *J. Clin. Invest.* 104:1165-1166.

Adeno-associated virus (AAV) vectors offer several potential advantages as vectors for the transfer of the CFTR gene to CF airway epithelial cells. First, they have an excellent safety record in the lab and in humans. Second, they target both dividing and non-dividing cells like those in airway epithelia. Third, they do not induce a cell-mediated immune response. Fourth, they have been reported to generate long-term transgene expression. Fifth, unlike adenovirus and other human AAV serotypes, serotype 5 of human AAV (AAV5) targets the apical surface of differentiated airway epithelia. See Zabner et al., 2000, *J. Virol.* 74:3852-3858.

The utility of AAV vectors for CF gene transfer, however, is limited by their packaging capacity. The single-stranded genome of AAV5 is 4642 bp in length, which is similar to that of other AAV serotypes (Chiorini et al., 1999, *J. Virol.* 73:1309-1319), making it likely that AAV vectors will package only relatively small genomes. The only cis components required for replication and packaging of the recombinant genome into AAV5 virions are the two AAV5 ITRs, each 167 bp in length. Rabinowitz et al., 2000, *Virology* 278:301-308. The full-length CFTR cDNA is 4443 bp in length from the ATG through the stop codon. Thus, the length of the ITRs and a full-length CFTR cDNA (4777 bp) exceeds the length of the wild-type AAV5 genome. Moreover, an AAV expression cassette must also include a promoter, an intervening sequence (IVS) between the transcription and translation start sites, and a poly(A) addition sequence. See FIG. 1 for a schematic representation showing a typical arrangement of these elements in an AAV expression cassette.

Dong et al. studied DNA of various sizes and concluded that the optimal packaging limit for the AAV2 serotype was 4.9 kb; above this limit, packaging efficiency dropped precipitously. Dong et al., 1996, *Human Gene Therapy* 7:2102-2112. This observation is consistent with the previous findings that AAV vectors containing transgene inserts substantially longer than 4.9 kb have been difficult to produce.

In general, vectors that contain cDNA encoding truncated CFTR with short promoters or encoding full-length CFTR with no promoter other than the ITR were packaged with varying efficiency. See Flotte et al., 1993, *J. Biol. Chem.* 268:3791-3790; Zhang et al., 1998, *Proc. Natl. Acad. Sci. USA* 95:10158-10163; Wang et al., 1999, *Gene Therapy* 6:667-675. Recombinant vectors longer than 4900 bp were packaged less efficiently or not at all.

For example, Flotte et al. found that a 5010 bp DNA encoding CFTR was not packaged. However, they were able to package a 4647 bp vector that contained cDNA encoding CFTR with residues 1-118 deleted. In this vector, the ITRs were used as a promoter. Flotte et al., 1993, *J. Biol. Chem.* 268:3791-3790. Similarly, Zhang et al. reported that they could package a 4837 bp sequence containing a full-length CFTR cDNA with no promoter other than the ITRs, but the vector generated no CFTR Cl-current. They also reported that a 4727 bp cassette with a p5 promoter and a CFTR containing deletions in both the C-terminus and the R domain generated Cl$^-$ current, as detected by the very sensitive patch-clamp technique in isolated cells. Zhang et al., 1998, *Proc. Natl. Acad. Sci. USA* 95:10158-10163. Wang et al. also produced a 4983 bp AAV vector with CFTR under control of the p5 promoter and reported detectable CFTR expression by whole-cell patch clamp in JME CF cells, but that genome was packaged much less efficiently than the 4837 bp genome of Zhang et al. Wang et al., 1999, *Gene Therapy* 6:667-675.

From these studies, it is clear that the relatively small packaging size limit of AAV vectors places severe constraints on the generation of AAV-based vectors for transfer of the CFTR cDNA. There are no reports of AAV-based vectors containing CFTR-encoding constructs longer than 5 kb. There are some reports of limited packaging into AAV virions for CFTR constructs of 4.9 and 5 kb in length. However, evidence that CFTR protein was expressed in cells transduced by these vectors relied on very sensitive patch-clamp detection techniques in single cells, and there was no evidence that expression was sufficient to generate trans-epithelial Cl$^-$ current in an epithelium.

The longest components contained within the AAV expression cassette (FIG. 1) are usually the promoter and the transgene. Thus, the two most likely ways in which the length of the expression cassette may be reduced would be to shorten the promoter or to shorten the transgene. The coding sequence of full length CFTR is 4450 bp. Riordan et al., 1989, *Science* 245:1066-1073. Addition of the two inverted terminal repeats of AAV (300 bp), and minimal 3' and 5' untranslated regions (~100 bp) yields an insert (4850 bp), which leaves little room for enhancer-promoter elements, most of which are >600 bp. However, several groups have shown that selective deletion of portions of the coding region of a gene can decrease the overall size of the gene while still allowing expression of an active protein molecule. This approach has been successfully employed to create a mini-dystrophin gene for use in gene therapy for Duchenne muscular dystrophy (DMD; Phelps et al., 1995, *Hum. Mol. Genet.* 4:1251-1258) and also for CFTR (Zhang et al., 1998, *Proc. Natl. Acad. Sci.* 95:10158-10163; and Flotte et al., 1993, *J. Biol. Chem.* 268: 3781-3790).

The R (regulatory) domain of the CFTR protein extends approximately from residues 634-708 at the N-terminus to approximately 835 at the C-terminus. See Ostedgaard et al., 2001, *J. Biol. Chem.* 276:7689-7692; Ostedgaard, et al., 2000, *Proc. Natl. Acad. Sci. U.S.A.* 97:5657-5662; and Csandy et al., 2000, *J. Gen. Physiol.* 116:477-500. Previous work has shown that a peptide encompassing residues 708-831 regulates activity, but in solution forms a predominantly random coil. Ostedgaard, et al., 2000, *Proc. Natl. Acad. Sci. U.S.A.* 97:5657-5662.

Several earlier studies showed that CFTR molecules in which portions of the R domain had been deleted still retained some CFTR function as a chloride ion channel. See Rich et al., 1991, *Science* 253:205-207; Rich et al., 1993, *Receptors Channels* 1:221-232; Ma et al., 1997, *J. Biol. Chem.* 272: 28133-28141; Zhang et al., 1998, *Proc. Natl. Acad. Sci. U.S.A.* 95:10158-10163; Vankeerberghen et al., 1999, *Biochemistry* 38:14988-14998; and Xie et al., 2000, *Biophys. J.* 78:1293-1305. However, at least some of these deletions induced channel activity in the absence of phosphorylation, reduced the response to PKA-dependent phosphorylation, and/or reduced net channel activity. See Rich et al., 1991, *Science* 253:205-207; Rich et al., 1993, *Receptors Channels* 1:221-232; Ma et al., 1997, *J. Biol. Chem.* 272:28133-28141; Zhang et al., 1998, *Proc. Natl. Acad. Sci. U.S.A.* 95:10158-10163; Vankeerberghen et al., 1999, *Biochemistry* 38:14988-14998; Xie et al., 2000, *Biophys. J.* 78:1293-1305; and Ostedgaard et al. 2001, *J. Biol. Chem.* 276:7689-7692. Moreover, previous studies have only examined CFTR expressed in heterologous cell lines and studied activity using the patch-clamp technique, planar lipid bilayers, or anion efflux. There was little information about their function in airway or other epithelia, which is critical in assessing the value of these proteins in gene transfer applications because deletions could alter protein-protein interactions, targeting to the apical membrane, constitutive and stimulated activity, phosphorylation-dependent regulation, and perhaps toxicity.

In contrast, Ostedgaard et al. have developed a shortened CFTR transgene (CFTR-ΔR) in which biosynthesis, localization, and Cl⁻ channel function of this CFTR-ΔR protein were demonstrated to be the same as wild-type CFTR in airway epithelia. Ostedgaard et al., 2002, *Proc. Natl. Acad. Sci. USA* 99:3093-3098. In these studies, however, an adenoviral vector, which has a much greater packaging capacity than AAV-based vectors, was employed to transfer the DNA sequence encoding the CFTR-ΔR into the airway epithelial cells. Incorporation of the same CFTR-ΔR expression cassette employed by Ostedgaard et al. into an AAV vector would still impose some packaging limitations. Thus, some truncation of the promoter sequence would still be necessary to achieve efficient rescue of this expression cassette in AAV vectors.

The cytomegalovirus immediate early (CMVie) enhancer-promoter is one of the most widely-employed promoters in gene transfer vectors. See Stinski, 1999, In *Gene Expression Systems: Using Nature for the Art of Expression.* Academic Press, New York. 1999. pp. 211-233. The CMVie enhancer-promoter directs expression in many different cell types, generates higher levels of expression than most other enhancer-promoters, and functions in many viral and non-viral vectors. For example, in the airway epithelial lines ELM and CFT1, the CMVie enhancer-promoter generated much greater expression of a reporter gene than promoters of a housekeeping gene (ubiquitin B), a cytokine gene (interleukin 8), a signaling ligand gene (nitric oxide synthase; NOS), the tissue-specific genes MUC1, CC10 and SPC, or another viral promoter (adenovirus E1a). Yew et al., 1997, *Human Gene Therapy* 8:575-584. Importantly, this relative expression pattern also was observed in vivo in mouse lung, and CMVie enhancer-promoter drives CFTR expression and corrects the CF Cl⁻ transport defect in cultured airway cell lines (JME/CF15) and primary cultures of differentiated airway epithelia. See Ostedgaard et al, 2002, *Proc. Natl. Acad. Sci. USA* 99:3093-3098; Jiang et al., 1996, *Am. J. Physiol.* 271:L527-L537. Forms of the CMVie enhancer truncated at nt −348 or nt −222 were observed to retain some activity. Stinski and Roehr, 1985, *J. Virol.* 55:431-441.

SUMMARY OF THE INVENTION

The present invention provides novel nucleic acid molecules for the regulation of gene transcription. These molecules are based on various functional truncated forms of the human cytomegalovirus immediate-early (CMVie) enhancer-promoter that promote expression of an operably-linked transgene.

In particular, the present invention provides functional truncated forms of the cytomegalovirus (CMV) immediate-early promoter that are useful in promoting the transcription of transgenes. Being relatively small in size, such promoters are especially useful in applications where the overall size of the expression cassette is a limiting factor, such as when AAV-based vectors are used to transfer genes with relatively long coding regions (i.e. those longer than approximately 3 to 4.5 kb). These truncated CMV promoters are therefore useful in the development of CFTR-expressing AAV vectors for use in gene therapy for CF.

In particular nonlimiting embodiments, the nucleic acid molecules of the present invention comprise functional variants of the human cytomegalovirus immediate-early enhancer-promoter region that are lacking the 16 and 21 base pair (bp) repeat units otherwise found in the wild-type human CMVie enhancer-promoter. The truncated CMVie enhancer-promoter elements of the present invention may contain one or more copies of the 18 and 19 bp repeat units present in the wild-type human CMVie enhancer-promoter. In particular nonlimiting embodiments, the nucleic acid molecules of the present invention comprise the nucleic acid sequence of SEQ ID NO:1 or SEQ ID NO:2. In specific nonlimiting embodiments, the nucleic acid molecules of the present invention are the nucleic acid sequence of SEQ ID NO:1 or SEQ ID NO:2.

In other nonlimiting embodiments, these truncated CMVie enhancer-promoter elements may be operably linked to a heterologous gene (i.e. a "transgene"), so that transcription of the transgene is regulated by the truncated CMVie enhancer-promoter elements of the present invention.

In particular nonlimiting embodiments, these truncated CMVie enhancer-promoter elements are operably linked to a transgene encoding a CFTR protein. In certain nonlimiting embodiments, the transgene encode CFTR proteins from which all or part of the R domain has been deleted. The CFTR-encoding transgenes operably linked to the truncated CMVie enhancer-promoter element may comprise, in addition to deletion of all or part of the R region, deletions in other regions provided that the proteins encoded by these transgenes exhibit functional chloride ion channel activity when expressed in a CF airway epithelia cell. In a particular non-limiting embodiment, the transgene encoding a CFTR protein from which all or part of the R domain has been deleted comprises the nucleic acid sequence of SEQ ID NO:3. In another specific nonlimiting embodiment, the transgene encoding a CFTR protein from which all or part of the R domain has been deleted consists essentially of the nucleic acid sequence of SEQ ID NO:3. In another specific nonlimiting embodiment, the transgene encoding a CFTR protein from which all or part of the R domain has been deleted is the nucleic acid sequence of SEQ ID NO:3.

Also provided are vectors comprising the nucleic acid molecules of the present invention. In particular nonlimiting embodiments, the vectors comprise nucleic acid molecules encoding functional variants of the human cytomegalovirus immediate-early enhancer-promoter region that lack the 16 and 21 bp repeat units, which are found in the wild-type human CMVie enhancer-promoter. In vectors of the present invention, the truncated CMVie enhancer-promoter elements may be operably linked to a transgene, including but not limited to a transgene encoding a CFTR protein from which all or part of the R domain has been deleted. In particular nonlimiting embodiments, the vectors of the present invention may comprise without limitation a cosmid, a phagemid, a bacteriophage, a bacterial artificial chromosome, a yeast artificial chromosome, a human artificial chromosome, a retrovirus vector, an adenovirus vector, an adeno-associated virus vector, a herpes virus vector, an Epstein-Barr virus vector, a vaccinia virus vector, or combinations or chimerics thereof. Those of ordinary skill in the art will recognize that the truncated CMVie enhancer-promoter elements of the present invention also will be useful in other vectors employed in the fields of gene expression and gene transfer, especially those in which the overall size of the transgene expression cassette is a limiting factor. In particular nonlimiting embodiments, the truncated CMVie enhancer-promoter elements of the present invention are incorporated into vectors derived from serotype 5 of human adeno-associated virus (AAV5).

The vectors of the present invention may further comprise various transgenes, intervening sequences, polyadenylation signals, and/or other elements known to those of ordinary skill in the art to express transgenes from certain vectors. In nonlimiting embodiments, the vectors of the present invention are derived from AAV5 that express a human CFTR protein or functional variants thereof. In other nonlimiting embodiments, the present invention provides vectors comprising a truncated CMVie enhancer-promoter elements, in accordance with the present invention, operably linked to other transgenes encoded by nucleic acid sequences greater than approximately 3 kb in length. In specific nonlimiting embodiments, the transgene is encoded by a nucleic acid sequence of approximately 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 kb in length.

Also provided by the present invention are cells transformed by the vectors described herein. In particular nonlimiting embodiments, transformed host cells include, but are not limited to, cultured airway epithelial cells, such as the A549 or H441 cell lines, primary airway epithelial cell cultures derived from CF or wild-type donors, or airway epithelial cells from CF or non-CF individuals in vivo et situ.

BRIEF DESCRIPTION OF THE FIGURES

FIG. 3. Nucleotide sequence of the 173CMV-CFTRΔR expression cassette. The NotI restriction endonuclease recognition sites are shown in the boxes. The CMV promoter region is shown in underlined type. The intervening sequence region is shown in bold, underlined type. The ATG translation initiation codon is shown in dashed underlining. The asterisks indicate the site of the R domain deletion. The TAG stop codon is shown in double underlining. The SPA sequence is shown in bold, double underlined type.

FIG. 4. Nucleotide sequence of the 113CMV-CFTRΔR expression cassette. The NotI restriction endonuclease recognition sites are shown in the boxes. The CMV promoter region is shown in underlined type. The intervening sequence region is shown in bold, underlined type. The ATG translation initiation codon is shown in dashed underlining. The asterisks indicate the site of the R domain deletion. The TAG stop codon is shown in double underlining. The SPA sequence is shown in bold, double underlined type.

FIG. 10. (A) Expression relative to CMVie.

DETAILED DESCRIPTION OF THE INVENTION

Figure 1:
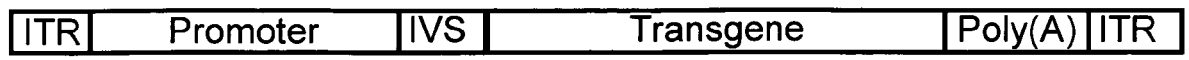
FIG. 1. Schematic representation of a typical arrangement of an AAV expression cassette. ITR represents the AAV inverted terminal repeat. IVS represents an intervening sequence located between the transcription and translation initiation sites. Poly(A) represents a polyadenylation signal sequence.
Figure 2:
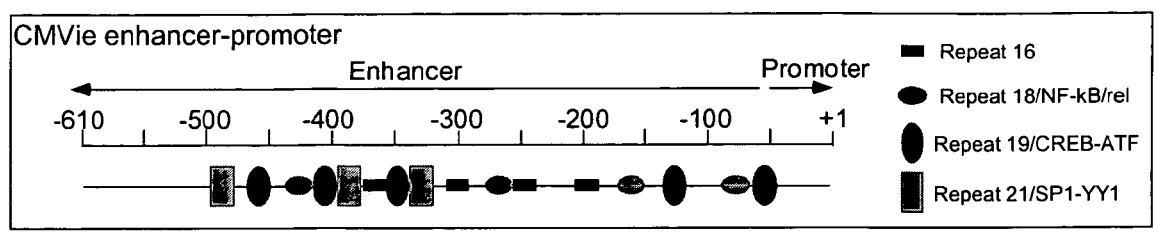
FIG. 2. Schematic representation of the cytomegalovirus immediate-early (CMVie) enhancer-promoter. Relative locations of identified transcription factor binding sites are indicated by the various symbols. The transcription start site is indicated as "+1."

The present invention is based on the surprising finding that the human cytomegalovirus immediate-early (CMVie) enhancer-promoter element, which in the wild-type form contains a constellation of 16, 18, 19 and 21 bp repeat units as depicted schematically in FIG. 2, may be truncated to remove completely the 16 and 21 bp repeat units without eliminating its activity as a transcriptional regulator. The relatively small sizes of the promoters created by the various truncations described herein make them well-suited for incorporation into transgene expression cassettes in which length is otherwise a limiting factor, for example when the transgene to be expressed is encoded by a gene or cDNA whose size is relatively large, i.e. greater than approximately 3 kb in length, and the vector to be used for delivery of the transgene has a relatively small packaging limit, e.g. adeno-associated viruses (AAV), which have a packaging limit of approximately 5 kb.

In particular nonlimiting embodiments, the truncated CMVie enhancer-promoter elements of the present invention have the following nucleic acid sequences:

```
                                            (SEQ ID NO: 1)
5'-ACTCACGGGGATTTCCAAGTCTCCACCCCATTGACGTCAATGGGAGT
TTGTTTTGGCACCAAAATCAACGGGACTTTCCAAAATGTCGTAATAACCC
CGCCCCGTTGACGCAAATGGGCGGTAGGCGTGTACGGTGGGAGGTCTATA
TAAGCAGAGCTCGTTTAGTGAACCGT-3',
or
                                            (SEQ ID NO: 2)
5'-AAAATCAACGGGACTTTCCAAAATGTCGTAATAACCCCGCCCCGTTG
ACGCAAATGGGCGGTAGGCGTGTACGGTGGGAGGTCTATATAAGCAGAGC
TCGTTTAGTGAACCGT-3',
``` corresponding to the truncated CMVie enhancer-promoters CMV173 and CMV113, respectively. However, those of ordinary skill in the art will recognize that the CMVie enhancer-promoters of the present invention are not limited merely to those of SEQ ID NO:1 and SEQ ID NO:2. Indeed, one of ordinary skill in the art will recognize that the present invention encompasses any and all promoters derived from the wild-type human CMVie enhancer-promoter that lack the 16 and 21 bp repeat units while retaining one or more copies of the 18 and 19 bp repeat units present in the wild-type human CMVie enhancer-promoter. Thus, the CMVie enhancer-promoters of the present invention include nucleic acid sequences in which nucleotide substitutions, deletions or insertions have been made, provided that these substitutions, deletions or insertions do not alter the sequences of the one or more copies of the 18 and 19 bp repeat units retained in the truncated CMVie enhancer-promoter, and further provided that these substitutions, deletions or insertions do not diminish the activity of the resulting promoter elements to less than approximately 10% of the activity of the CMVie enhancer-promoters of SEQ ID NOS:1 or 2. A person of ordinary skill in the art would appreciate that the strength of a given promoter could be readily determined using any one of a number of standard reporter gene assays including, but not limited to, a β-galactosidase reporter gene assay such as that employed in Example 1 below.

In further embodiments, the truncated CMVie enhancer-promoter elements of the present invention may be operably linked to a heterologous gene (i.e. a "transgene"), so that transcription of the transgene is regulated by a truncated CMVie enhancer-promoter element. In particular nonlimiting embodiments, the truncated CMVie enhancer-promoter elements of the present invention are be operably linked to a transgene encoding a CFTR protein. In other nonlimiting embodiments, the truncated CMVie enhancer-promoter elements of the present invention are operably linked to a transgene encoding a CFTR protein from which all or part of the R domain has been deleted. The CFTR-encoding transgene operably linked to the truncated CMVie enhancer-promoter element may comprise, in addition to deletion of all or part of the R region, deletions in other regions provided that the protein encoded by the transgene produces functional chloride ion channel activity when expressed in CF airway epithelia cells. In a specific nonlimiting embodiment, the transgene encoding a CFTR protein from which all or part of the R domain has been deleted comprises one of the following nucleic acid sequences:

```
                                            (SEQ ID NO: 3)
5'-ATGCAGAGGTCGCCTCTGGAAAAGGCCAGCGTTGTCTCCAAACTTTT

TTTCAGCTGGACCAGACCAATTTTGAGGAAAGGATACAGACAGCGCCTGG

AATTGTCAGACATATACCAAATCCCTTCTGTTGATTCTGCTGACAATCTA

TCTGAAAAATTGGAAAGAGAATGGGATAGAGAGCTGGCTTCAAAGAAAAA

TCCTAAACTCATTAATGCCCTTCGGCGATGTTTTTTCTGGAGATTTATGT

TCTATGGAATCTTTTTATATTTAGGGGAAGTCACCAAAGCAGTACAGCCT

CTCTTACTGGGAAGAATCATAGCTTCCTATGACCCGGATAACAAGGAGGA

ACGCTCTATCGCGATTTATCTAGGCATAGGCTTATGCCTTCTCTTTATTG

TGAGGACACTGCTCCTACACCCAGCCATTTTTGGCCTTCATCACATTGGA

ATGCAGATGAGAATAGCTATGTTTAGTTTGATTTATAAGAAGACTTTAAA

GCTGTCAAGCCGTGTTCTAGATAAAATAAGTATTGGACAACTTGTTAGTC

TCCTTTCCAACAACCTGAACAAATTTGATGAAGGACTTGCATTGGCACAT

TTCGTGTGGATCGCTCCTTTGCAAGTGGCACTCCTCATGGGGCTAATCTG

GGAGTTGTTACAGGCGTCTGCCTTCTGTGGACTTGGTTTCCTGATAGTCC

TTGCCCTTTTTCAGGCTGGGCTAGGGAGAATGATGATGAAGTACAGAGAT

CAGAGAGCTGGGAAGATCAGTGAAAGACTTGTGATTACCTCAGAAATGAT

TGAAAATATCCAATCTGTTAAGGCATACTGCTGGGAAGAAGCAATGGAAA

AAATGATTGAAAACTTAAGACAAACAGAACTGAAACTGACTCGGAAGGCA

GCCTATGTGAGATACTTCAATAGCTCAGCCTTCTTCTTCTCAGGGTTCTT

TGTGGTGTTTTTATCTGTGCTTCCCTATGCACTAATCAAAGGAATCATCC
```

-continued

TCCGGAAAATATTCACCACCATCTCATTCTGCATTGTTCTGCGCATGGCG

GTCACTCGGCAATTTCCCTGGGCTGTACAAACATGGTATGACTCTCTTGG

AGCAATAAACAAAATACAGGATTTCTTACAAAAGCAAGAATATAAGACAT

TGGAATATAACTTAACGACTACAGAAGTAGTGATGGAGAATGTAACAGCC

TTCTGGGAGGAGGGATTTGGGGAATTATTTGAGAAAGCAAAACAAAACAA

TAACAATAGAAAAACTTCTAATGGTGATGACAGCCTCTTCTTCAGTAATT

TCTCACTTCTTGGTACTCCTGTCCTGAAAGATATTAATTTCAAGATAGAA

AGAGGACAGTTGTTGGCGGTTGCTGGATCCACTGGAGCAGGCAAGACTTC

ACTTCTAATGATGATTATGGGAGAACTGGAGCCTTCAGAGGGTAAAATTA

AGCACAGTGGAAGAATTTCATTCTGTTCTCAGTTTTCCTGGATTATGCCT

GGCACCATTAAAGAAAATATCATCTTTGGTGTTTCCTATGATGAATATAG

ATACAGAAGCGTCATCAAAGCATGCCAACTAGAAGAGGACATCTCCAAGT

TTGCAGAGAAAGACAATATAGTTCTTGGAGAAGGTGGAATCACACTGAGT

GGAGGTCAACGAGCAAGAATTTCTTTAGCAAGAGCAGTATACAAAGATGC

TGATTTGTATTTATTAGACTCTCCTTTTGGATACCTAGATGTTTTAACAG

AAAAAGAAATATTTGAAAGCTGTGTCTGTAAACTGATGGCTAACAAAACT

AGGATTTTGGTCACTTCTAAAATGGAACATTTAAAGAAAGCTGACAAAAT

ATTAATTTTGCATGAAGGTAGCAGCTATTTTTATGGGACATTTTCAGAAC

TCCAAAATCTACAGCCAGACTTTAGCTCAAAACTCATGGGATGTGATTCT

TTCGACCAATTTAGTGCAGAAAGAAGAAATTCAATCCTAACTGAGACCTT

ACACCGTTTCTCATTAGAAGGAGATGCTCCTGTCTCCTGGACAGAAACAA

AAAAACAATCTTTTAAACAGACTGGAGAGTTTGGGGAAAAAAGGAAGAAT

TCTATTCTCAATCCAATCAACTCTACGCTTCAGGCACGAAGGAGGCAGTC

TGTCCTGAACCTGATGACACACTCAGTTAACCAAGGTCAGAACATTCACC

GAAAGACAACAGCATCCACACGAAAAGTGTCACTGGCCCCTCAGGCAAAC

TTGACTGAACTGGATATATATTCAAGAAGGTTATCTCAAGAAACTGGCTT

GGAAATAAGTGAAGAAATTAACGAAGAAGACTTAAAGGAGTGCTTTTTTG

ATGATATGGAGAGCATACCAGCAGTGACTACATGGAACACATACCTTCGA

TATATTACTGTCCACAAGAGCTTAATTTTTGTGCTAATTTGGTGCTTAGT

AATTTTTCTGGCAGAGGTGGCTGCTTCTTTGGTTGTGCTGTGGCTCCTTG

GAAACACTCCTCTTCAAGACAAAGGGAATAGTACTCATAGTAGAAATAAC

AGCTATGCAGTGATTATCACCAGCACCAGTTCGTATTATGTGTTTTACAT

TTACGTGGGAGTAGCCGACACTTTGCTTGCTATGGGATTCTTCAGAGGTC

TACCACTGGTGCATACTCTAATCACAGTGTCGAAAATTTTACACCACAAA

ATGTTACATTCTGTTCTTCAAGCACCTATGTCAACCCTCAACACGTTGAA

AGCAGGTGGGATTCTTAATAGATTCTCCAAAGATATAGCAATTTTGGATG

ACCTTCTGCCTCTTACCATATTTGACTTCATCCAGTTGTTATTAATTGTG

ATTGGAGCTATAGCAGTTGTCGCAGTTTTACAACCCTACATCTTTGTTGC

AACAGTGCCAGTGATAGTGGCTTTTATTATGTTGAGAGCATATTTCCTCC

AAACCTCACAGCAACTCAAACAACTGGAATCTGAAGGCAGGAGTCCAATT

-continued

TTCACTCATCTTGTTACAAGCTTAAAAGGACTATGGACACTTCGTGCCTT

CGGACGGCAGCCTTACTTTGAAACTCTGTTCCACAAAGCTCTGAATTTAC

ATACTGCCAACTGGTTCTTGTACCTGTCAACACTGCGCTGGTTCCAAATG

AGAATAGAAATGATTTTTGTCATCTTCTTCATTGCTGTTACCTTCATTTC

CATTTTAACAACAGGAGAAGGAGAAGGAAGAGTTGGTATTATCCTGACTT

TAGCCATGAATATCATGAGTACATTGCAGTGGGCTGTAAACTCCAGCATA

GATGTGGATAGCTTGATGCGATCTGTGAGCCGAGTCTTTAAGTTCATTGA

CATGCCAACAGAAGGTAAACCTACCAAGTCAACCAAACCATACAAGAATG

GCCAACTCTCGAAAGTTATGATTATTGAGAATTCACACGTGAAGAAAGAT

GACATCTGGCCCTCAGGGGGCCAAATGACTGTCAAAGATCTCACAGCAAA

ATACACAGAAGGTGGAAATGCCATATTAGAGAACATTTCCTTCTCAATAA

GTCCTGGCCAGAGGGTGGGCCTCTTGGGAAGAACTGGATCAGGGAAGAGT

ACTTTGTTATCAGCTTTTTTGAGACTACTGAACACTGAAGGAGAAATCCA

GATCGATGGTGTGTCTTGGGATTCAATAACTTTGCAACAGTGGAGGAAAG

CCTTTGGAGTGATACCACAGAAAGTATTTATTTTTTCTGGAACATTTAGA

AAAAACTTGGATCCCTATGAACAGTGGAGTGATCAAGAAATATGGAAAGT

TGCAGATGAGGTTGGGCTCAGATCTGTGATAGAACAGTTTCCTGGGAAGC

TTGACTTTGTCCTTGTGGATGGGGGCTGTGTCCTAAGCCATGGCCACAAG

CAGTTGATGTGCTTGGCTAGATCTGTTCTCAGTAAGGCGAAGATCTTGCT

GCTTGATGAACCCAGTGCTCATTTGGATCCAGTAACATACCAAATAATTA

GAAGAACTCTAAAACAAGCATTTGCTGATTGCACAGTAATTCTCTGTGAA

CACAGGATAGAAGCAATGCTGGAATGCCAACAATTTTTGGTCATAGAAGA

GAACAAAGTGCGGCAGTACGATTCCATCCAGAAACTGCTGAACGAGAGGA

GCCTCTTCCGGCAAGCCATCAGCCCCTCCGACAGGGTGAAGCTCTTTCCC

CACCGGAACTCAAGCAAGTGCAAGTCTAAGCCCCAGATTGCTGCTCTGAA

AGAGGAGACAGAAGAAGAGGTGCAAGATACAAGGCTTTAG-3'.

In other specific, nonlimiting embodiments, the transgene encoding a CFTR protein comprises a CFTR protein in which amino acids 708-835, amino acids 708-759, amino acids 708-723, 749-783 and 832-835, amino acids 708-723, 749-783 and 819-835, amino acids 708-759 and 819-835, amino acids 760-835, amino acids 708-783, or amino acids 708-783 and 823-835 have been deleted. In other specific, nonlimiting embodiments, the CFTR protein consists essentially of one of these CFTR variants. In a specific, nonlimiting embodiment, the CFTR protein consists essentially of SEQ ID NO:3.

Non-CFTR transgenes whose transcription also may be regulated by the CMVie enhancer-promoter elements of the present invention may include any transgene of interest in gene transfer or gene therapy applications, such as those for the treatment of metabolic disorders, infectious diseases, acquired diseases, or oncogenic diseases. See e.g. U.S. Pat. No. 5,872,005. The enhancer-promoter elements of the present invention are particularly useful in regulating transcription of transgenes containing relatively long coding regions (i.e. regions longer than approximately 3 to 4.5 kb). One example of a gene with a relatively long coding region that is of importance in gene therapy applications is the dystrophin gene, the cDNA of which is approximately 14 kb in length. Those of ordinary skill in the art will recognize other gene expression or gene transfer applications that would potentially benefit from the application of the truncated CMVie enhancer-promoters of the present invention.

The present invention also provides for vectors comprising nucleic acid molecules of the invention including, without limitation, nucleic acid molecules comprising the truncated CMVie enhancer-promoter elements lacking the 16 and 21 bp repeat units otherwise found in the wild-type human CMVie enhancer-promoter. In these vectors, the truncated CMVie enhancer-promoter elements may be operably linked to a transgene, such as those discussed immediately above. In particular nonlimiting embodiments, these vectors comprise the truncated CMVie enhancer-promoter elements operably linked to a transgene encoding a CFTR protein from which all or part of the R domain has been deleted. In particular nonlimiting embodiments, these vectors comprise truncated CMVie enhancer-promoter elements operably linked to transgenes having the nucleic acid sequence of SEQ ID NO:3, or encoding CFTR proteins from which amino acids 708-835, amino acids 708-759, amino acids 708-723, 749-783 and 832-835, amino acids 708-723, 749-783 and 819-835, amino acids 708-759 and 819-835, amino acids 760-835, amino acids 708-783, or amino acids 708-783 and 823-835 have been deleted.

In further embodiments, vectors comprising the truncated CMVie enhancer-promoter elements of the present invention may include, but are not limited to, a plasmid, a cosmid, a phagemid, a bacteriophage, a bacterial artificial chromosome, a yeast artificial chromosome, a human artificial chromosome, a retrovirus vector, a lentivirus vector, an adenovirus vector, an adeno-associated virus vector, a herpes virus vector, an Epstein-Barr virus vector, an alphavirus, or a vaccinia virus vector. Those of ordinary skill in the art will recognize that the truncated CMVie enhancer-promoter elements of the present invention also will be useful in other vectors employed in the fields of gene expression and gene transfer, especially those in which the overall size of the transgene expression cassette is a limiting factor. In particular nonlimiting embodiments, the truncated CMVie enhancer-promoter elements of the present invention are incorporated into vectors derived from human adeno-associated virus (AAV), especially vectors derived from serotype 5 of human AAV (AAV5).

The vectors of the present invention may further comprise various transgenes, intervening sequences, polyadenylation signals, or other elements known to those of ordinary skill in the art to be beneficial to the expression of transgenes from the particular vector being examined. Particularly preferred are vectors derived from AAV5 that express human CFTR protein or functional variants thereof. Alternative vector embodiments may include those in which the truncated CMVie enhancer-promoter elements of the present invention are operably linked to other transgenes encoded by nucleic acid sequences greater than approximately 3 kb in length.

Also provided by the present invention are cells transformed by the vectors described herein. In this context, transformation refers to any process by which heterologous nucleic acid material is introduced into and expressed within a cell. Thus, transformation as used herein includes "transient" transfection procedures, including but not limited to those mediated by electroporation, cationic lipid/DNA complexes, protein/DNA complexes, calcium phosphate-mediated pinocytosis, virus vectors, etc., where a nucleic acid introduced into the host cell exists extrachromosomally. Moreover, transformation as used herein may refer to so-called "stable" transfection methods, wherein a particular nucleic acid is introduced into a host cell in combination with a second nucleic acid encoding a selectable marker (e.g. resistance to an antibiotic), which enables the positive selection of cells in which the transfected nucleic acids have been integrated into the genome of the host cell. In particular nonlimiting embodiments, such vector-transformed cells include, but are not limited to, cultured airway epithelial cells, such as the A549 or H441 cell lines, primary airway epithelial cell cultures derived from CF or wild-type donors, or airway epithelial cells from CF or non-CF individuals in vivo et situ.

The present invention provides methods for treating genetic, metabolic or acquired diseases. In a nonlimiting embodiment, the present invention provides a method for expressing a nucleic acid molecule of the invention in a cell, the method comprising contacting the cell with a sufficient amount of a nucleic acid molecule and/or vector of the present invention. Preferably, the method is performed under conditions in which the transgene of interest is expressed in the cell. The transgene-expressing cell may be transduced with the transgene in vitro, ex vivo, or in vivo.

In another nonlimiting embodiment, the present invention provides a method for treating a subject having, or at risk of having, cystic fibrosis (CF) airway disease, the method comprising contacting the subject in need of such treatment with a sufficient amount of a nucleic acid molecule, vector, and/or cell of the present invention. Preferably, the treatment is performed under conditions in which the transgene of interest is expressed in the subject. The nucleic acid molecule, vector, and/or cell of the present invention may be contacted with the cells or tissues of the subject by any suitable mode of administration. For example, a vector of the invention may be administered topically on differentiated airway epithelia. In another example, a vector of the invention may be administered topically on the apical membrane of an epithelial cell. In yet another example, a nucleic acid molecule and/or vector of the present invention may be contacted with the cells or tissues of the subject by intranasal administration. The subject may be mammalian, preferably human. The effectiveness of the treatment may be assayed using any suitable method available to one of ordinary skill in the art.

In particular nonlimiting embodiments, the present invention provides methods for treating a subject with cystic fibrosis (CF) airway disease. The method may comprise contacting the subject in need of such treatment with a sufficient amount of a vector, wherein the vector comprises a nucleic acid having a functional truncated human cytomegalovirus immediate-early enhancer-promoter region, wherein the full-length human cytomegalovirus immediate-early enhancer-promoter region comprises nucleotide repeat units of 16, 18, 19 and 21 base pairs, wherein said truncated human cytomegalovirus immediate-early enhancer-promoter lacks the nucleotide repeat units of 16 and 21 base pairs, wherein the nucleic acid is operably linked to a transgene, and wherein the transgene expresses in the subject a nucleic acid molecule encoding a CFTR protein having a deletion in the R domain.

The present invention is further illustrated by the following examples which in no way should be construed as further limiting the invention.

EXAMPLES

Example 1

Construction and Analysis of Truncated CMVie Enhancer-promoters

FIG. 2 shows a diagram of the 610-bp human CMVie enhancer-promoter, which contains clusters of nucleotide repeats that bind specific transcription factors. Stinski, 1999, In *Gene Expression Systems: Using Nature for the Art of Expression*. Academic Press, New York. 1999. pp. 211-233. Coordination between these transcription factors determines promoter activity. To maintain promoter activity while reducing length, sequences that contained different combinations of these nucleotide clusters were systematically removed and inserted into a β-galactosidase reporter plasmid. The resulting plasmids then were transfected into two airway epithelial cell lines (A549 and H441) and into non-polarized, primary cultures of human airway epithelial cells by lipofectamine-mediated transfection, where promoters that were functional in airway epithelia could be identified.

Figure 5:
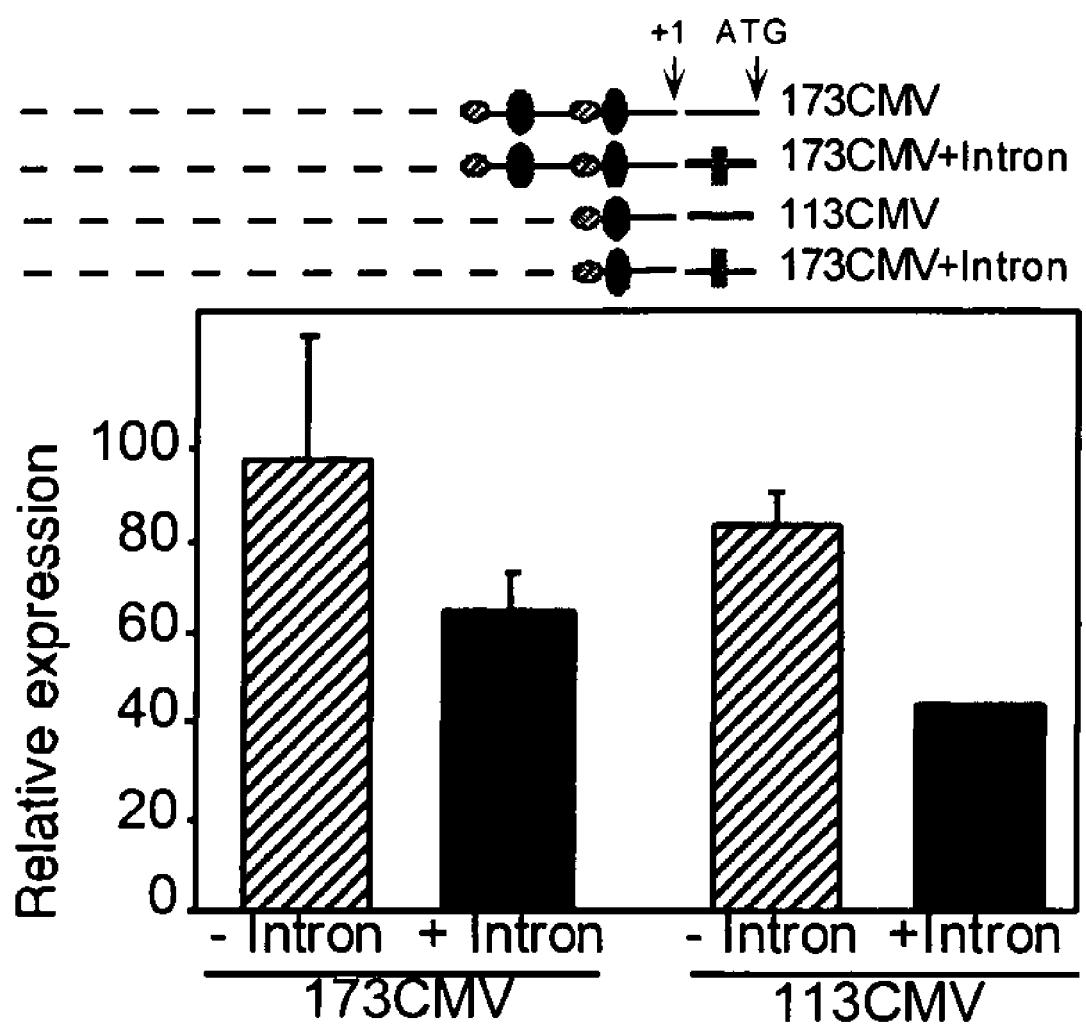
FIG. 5. Effect of the presence or absence of an intron on expression in A549 cells of a β-galactosidase gene driven by a CMVie promoter truncated as indicated. Expression is presented as β-galactosidase activity of the indicated construct relative to that obtained from the full-length CMVie enhancer-promoter.

The initial constructs examined were the CMVie enhancer-promoter truncated at nt −348 or −222 previously studied by Stinski. Stinski and Roehr, 1985, *J. Virol*. 55:431-441. These constructs produced β-galactosidase activity in all airway cells tested. Shorter promoter constructs that retained either two pairs of the 18-bp and 19-bp repeats (173CMV) or a single set of the 18-bp and 19-bp repeats (113CMV) then were examined. The nucleotide sequences of 173CMV and 113CMV are shown within the context of a complete expression cassette in FIGS. 3 and 4, respectively. As shown in FIG. 5, when expressed in the airway cell lines and in primary cultures of airway epithelia, these two shortened constructs maintained much of the high-level expression of the full-length CMVie.

Example 2

Effect of an Intervening Sequence on the Function of the Truncated CMVie Enhancer-promoters In previous studies utilizing the full-length CMVie enhancer-promoters, it was observed that the inclusion of an intron increased expression levels. Yew et al., 1997, *Human Gene Therapy* 8:575-584. Therefore, the effect of including the 19S/16S intron from SV40 in the intervening sequence between the transcription and translation start sites of the 173CMV and 113CMV constructs were examined. As shown in FIG. 5, this intron did not enhance β-galactosidase activity in A549 cells, but instead slightly reduced promoter activity.

Figure 6:
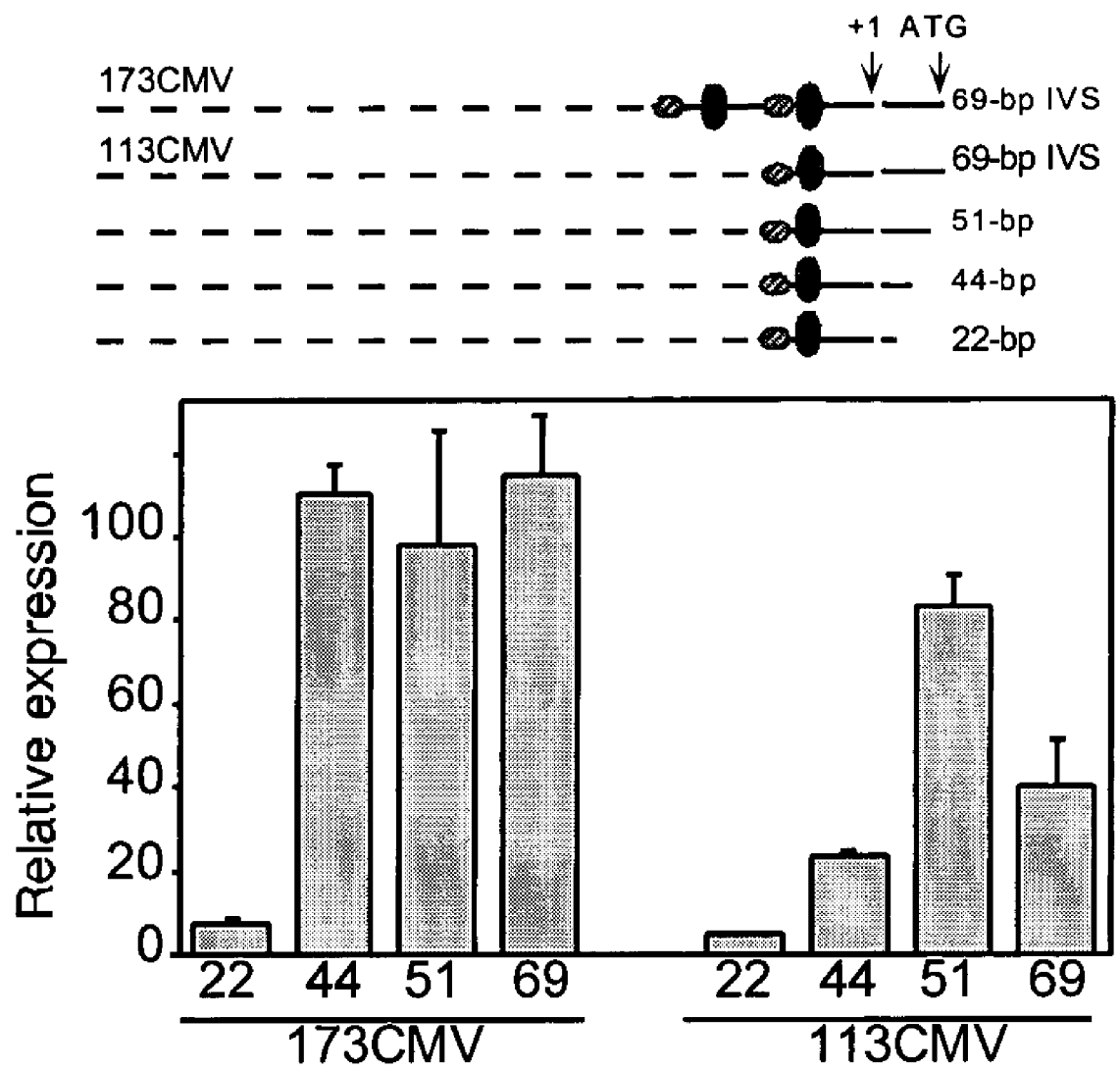
FIG. 6. Effect of length of intervening sequence on expression in A549 cells of a β-galactosidase gene driven by a CMV promoter truncated as indicated followed by an intervening sequence (IVS) of 22, 44, 51, or 69 bp. Expression is presented as β-galactosidase activity of the indicated construct relative to that obtained from the full-length CMVie enhancer-promoter followed by a 51 bp IVS.

To determine how the length of the intervening sequence (IVS) between the transcriptional and translational start sites affected promoter activity, a series of IVSs of differing lengths that maintain a minimum of predicted secondary structure were examined. The IVS in our original vector was 69-bp and was a composite of a multiple cloning site and the 5' untranslated region upstream of the β-galactosidase coding sequence (from the Clontech plasmid pCMVβ). For both the 173CMV and 113CMV promoters, the effect of varying the length of the IVS on the relative β-galactosidase expression was tested. As shown in FIG. 6, a 22-bp IVS with no Kozak sequence markedly reduced expression. When the IVS included the Kozak translation consensus sequence, length had little effect on expression from the 173CMV promoter. In contrast, in the 113CMV promoter, a 51-bp IVS generated substantially more activity than either a longer 69-bp or a shorter 44-bp IVS.

Example 3

Figure 7:
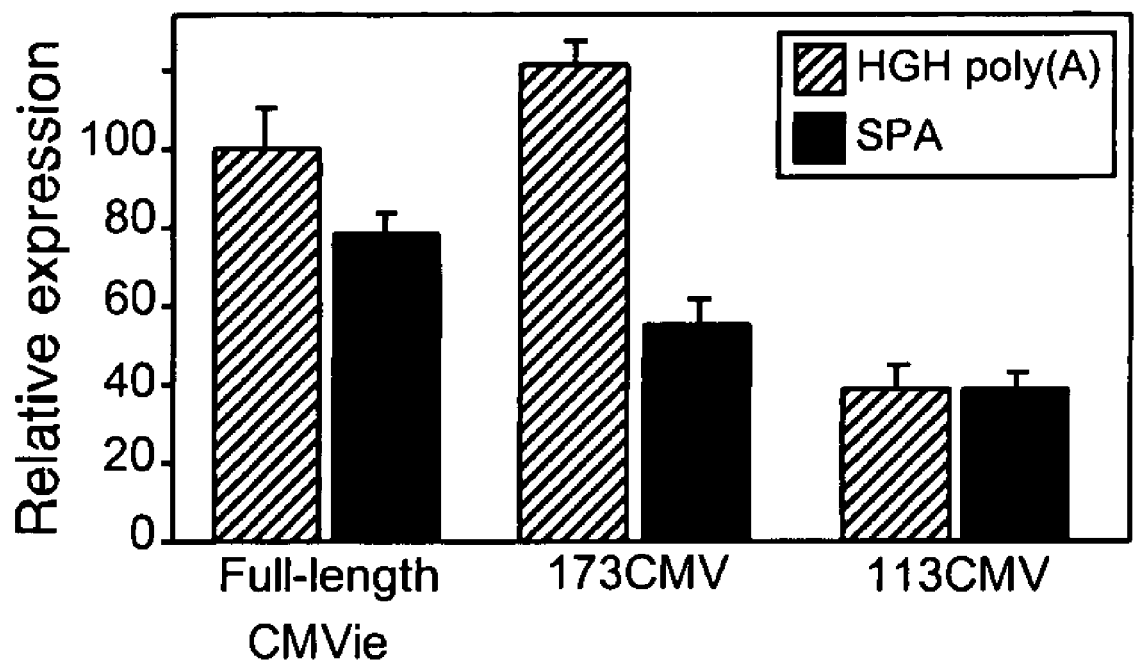
FIG. 7. Effect of replacement of the human growth hormone poly(A) tail by a synthetic polyadenylation signal sequence on expression in A549 cells of a β-galactosidase gene driven by full-length and truncated CMVie enhancer-promoters. Expression is presented as β-galactosidase activity of the indicated construct relative to that obtained from the full-length CMVie enhancer-promoter with a full-length hGH poly(A) tail.

Effect of Polyadenylation Signals on the Function of the Truncated CMVie Enhancer-promoters The 49-bp consensus synthetic poly(A) addition (SPA) sequence (AATAAA(22nt)GTx/Tx) has been reported to be equivalent to or better than a typical full-length poly(A) addition sequence in expression constructs. Levitt et al., 1989, *Genes Dev*. 3:1019-1025. To determine whether this SPA could replace the full-length 630-bp human growth hormone (hGH) poly(A) sequence present in pCMV5-β-gal, constructs containing these two alternative poly(A) signals were prepared and tested in airway epithelial cell cultures. As shown in FIG. 7, these two poly(A) addition signals yielded nearly equivalent expression levels when tested with the full-length CMVie and the 113CMV promoters. However, expression from the 173CMV promoter was reduced when the SPA was used.

Example 4

Construction and Testing of AAV5-based Vectors Incorporating the Truncated CMVie Enhancer-promoters Based on these results, two AAV expression cassettes were prepared, one with the 173-bp CMVie truncated enhancer-promoter (SEQ ID NO:1) and a second one with the 113-bp CMVie truncated enhancer-promoter (SEQ ID NO:2). The nucleotide sequences of these expression cassettes are depicted in FIGS. 3 and 4, respectively. The enhancer-promoter sequences were ligated directly to the AAV5 ITR sequence (167 bp), resulting in the retention of only minimal plasmid sequences (26 bp of plasmid sequence and 8 bp corresponding to the NotI restriction endonuclease recognition site; see Table 1). The expression cassette included the 51-bp IVS followed by the CFTRΔR transgene (SEQ ID NO:3) and the 49-bp SPA (Table 1 and FIGS. 3 and 4). The 173CMV expression cassette was 4940 bp in length and the 113CMV expression cassette was 4880 bp in length (Table 1).

Figure 8:
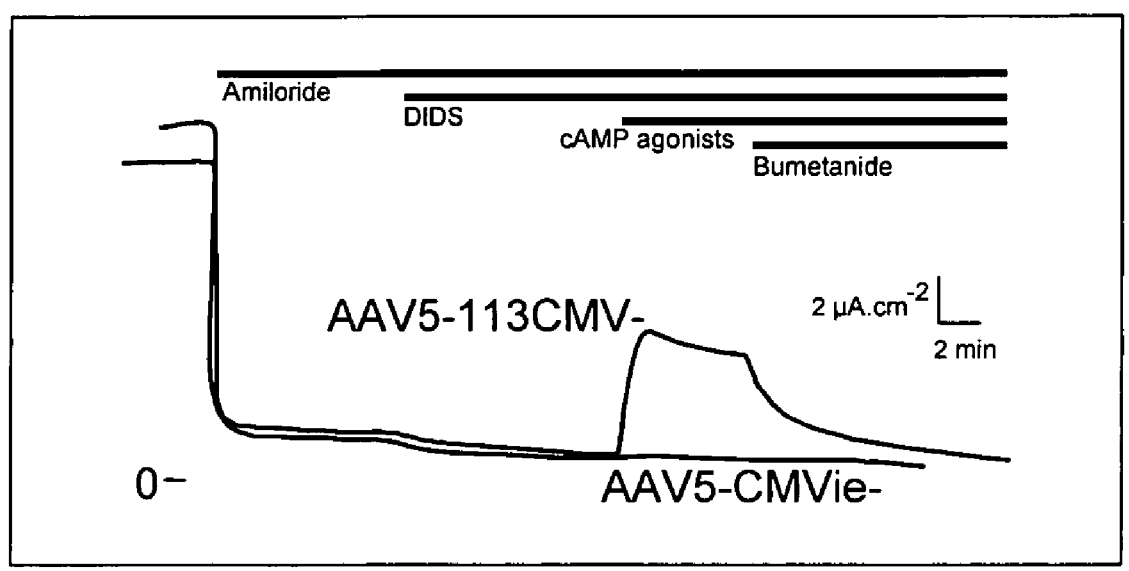
FIG. 8. Short-circuit current ($I_{SC}$) tracings from differentiated CF epithelia treated two weeks after treatment by an AAV5 vector, at a multiplicity of infection (MOI) of 10, containing either a full-length CMVie promoter driving GFP or a shortened 113-bp CMV promoter driving CFTR-ΔR. During the times indicated by the bars, the following agents were present: 100 μM mucosal amiloride, 100 μM mucosal DIDS, 10 μM forskolin and 100 μM IBMX (cAMP agonists), and 100 μM submucosal bumetanide.

These two expression cassettes were used to test the hypothesis that an AAV5 vector containing an cassette in which transcription of the CFTR-ΔR gene was regulated by a truncated CMVie enhancer-promoter could correct the Cl⁻ transport defect when applied to the apical surface of well differentiated CF airway epithelia. AAV5 viral vectors containing these expression cassettes were rescued and applied to the apical surface of CF airway epithelia, where they partially corrected the CF Cl-transport defect. FIG. 8 shows an example of a short-circuit current trace taken 2 weeks after applying 10 MOI, as determined by an infectious center assay (Hernandez et al., 1999, *J. Virol*. 73:8549-8558), of an AAV5 vector to the apical surface of an airway epithelium. The ratio of particles to infectious particles was ~1000:1. Transepithelial current in the vector-transduced cells increased with cAMP agonists and then fell when transepithelial current was blocked by bumetanide (FIG. 8).

Figure 9:
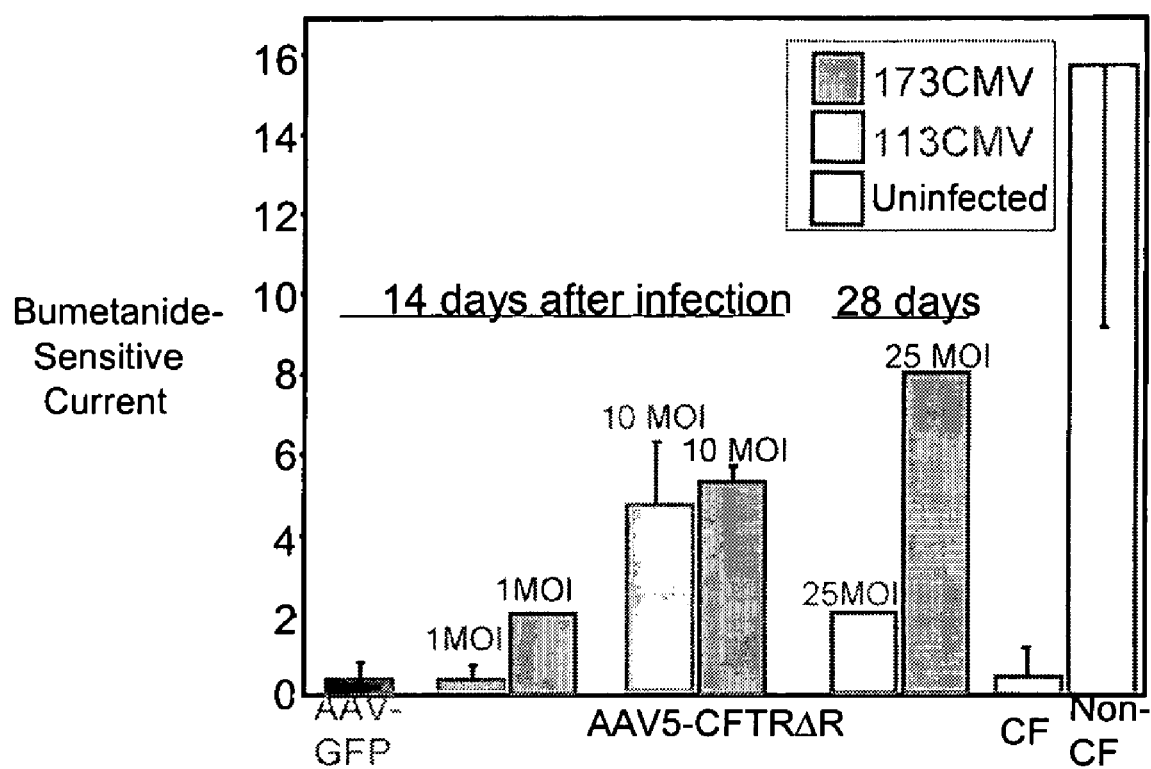
FIG. 9. Short circuit current ($I_{SC}$) following addition of bumetanide to inhibit trans-epithelial Cl⁻ transport. AAV5 vectors were applied to apical surface of differentiated CF epithelia for 30 minutes and trans-epithelial current was measured 2 weeks later. Data on the right in open bars are means±SD of cAMP-stimulated bumetadine-sensitive current from untreated CF (n-=64) and non-CF (n=458) epithelia. The data show that both short CMV promoters direct expression of cAMP-regulated CFTR channels in airway epithelia 14 days and 28 days following infection.
Figure 10A:
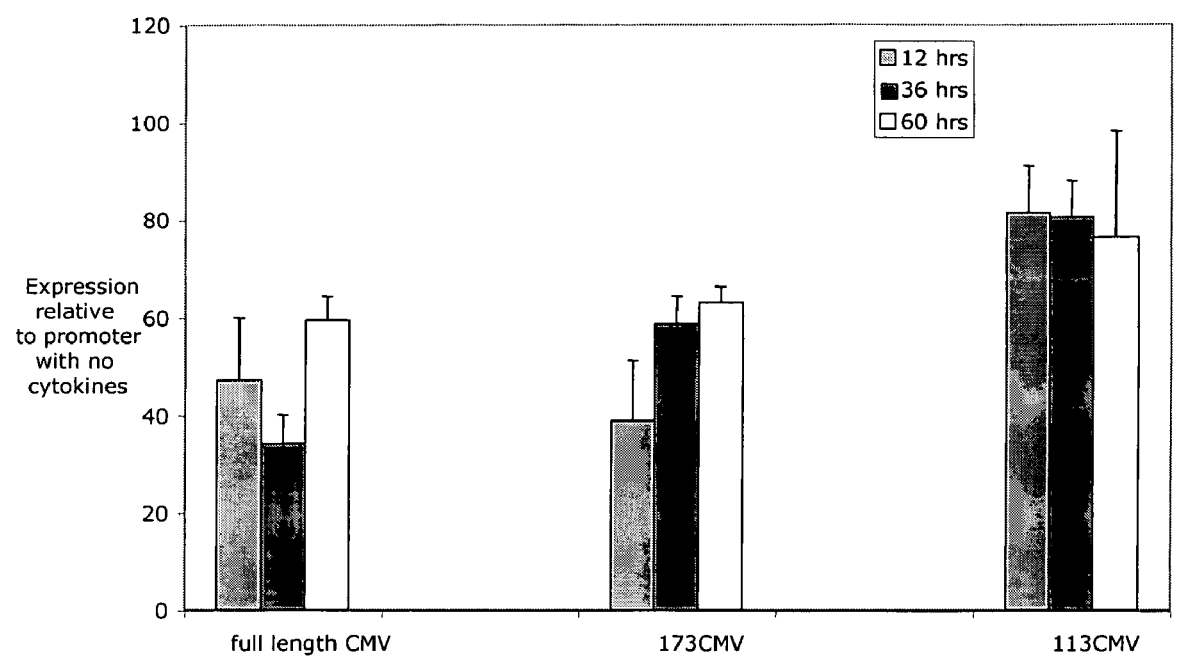
FIG. 10A shows beta-gal expression relative to that seen with a full length CMV promoter in the airway cell line A549 in the presence and in the absence of two cytokines, TNF-alpha (10 ng/ml) and IL-1beta (50 ng/ml) at 12, 36 and 60 hours after addition of cytokines. (B) Expression relative to promoter with no cytokines.
Figure 10B:
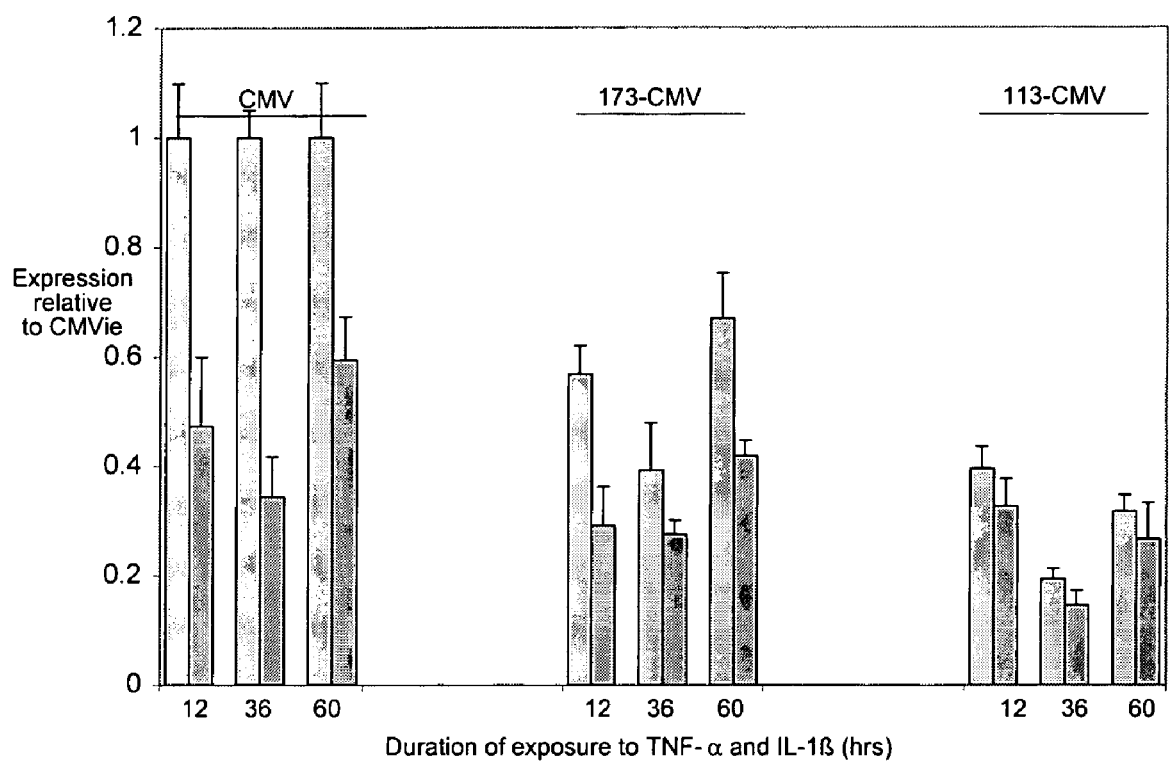
FIG. 10B shows beta-galactosidase expression in the presence of cytokines relative to each individual promoter without cytokine. The data indicate that cytokine downregulation of CMV-promoter-driven beta-galactosidase expression from either of the short CMV promoters is not greater than that observed using the full length CMV promoter.

As shown in FIG. 9, the amount of current produced in the transduced epithelia was dose-dependent, with transduction by 10 MOI of vector producing significantly greater amounts of conductance that transduction by 1 MOI. Average currents from a large number of CF and non-CF airway epithelia are shown at the right of FIG. 9 for purposes of comparison. As can be seen, transduction by 10 MOI of the AAV vectors in which either the 173CMV or 113CMV truncated enhancer-promoter elements were used to drive the transcription of the CFTR-ΔR gene restored approximately 30% of the amount of conductance observed in non-CF epithelia. These findings indicate that an AAV5 vector with a shortened promoter and transgene can partially correct the Cl⁻ transport defect when applied to the apical surface of well-differentiated CF airway epithelia (for example, by restoring approximately 30%, 40%, 50%, 60%, 70%, 80%, or 90% of the amount of conductance observed in non-CF epithelia). These studies provide the first evidence that an AAV vector can express functional CFTR in differentiated CF airway epithelia.

Example 5

Expression in Human Tissue Cultures of Adenoviral-based Vectors Incorporating Truncated CMVie Enhancer-promoters Cultures of human airway epithelia are obtained from CF bronchus and/or trachea (e.g., Delta F508/Delta F508 or Delta F508/other genotypes) and cultured at the air-liquid interface. Epithelia are used at least 14 days after seeding when they are well differentiated, e.g., epithelia comprising ciliated cells, goblet cells, and other nonciliated cells. Preferably, the epithelia retain certain functional properties of airway epithelia such as, for example, trans-epithelial electrolyte transport and resistance.

Epithelia are infected with multiplicities (e.g., 50, 100, 200, 500) of infection of adenoviral vectors of the invention using 5 mM EGTA applied to the apical surface to transiently disrupt the tight junctions as described.

Example 6

Expression in CF Mice of Adenoviral-based Vectors Incorporating Truncated CMVie Enhancer-promoters For in vivo analysis in animals, 6- to 8-wk-old Delta F508 homozygote CF mice are used. Mice are lightly anesthetized in a halothane chamber. Adenoviral vectors of the invention (e.g., $10^8$ particles, $10^9$ particles, $5 \times 10^9$ particles, $10^{10}$ particles) are administered intranasally as Ad:CaPi coprecipitates in two 5-µl instillations delivered 5 min apart. The adenoviral vector may encode a partially-deleted CFTR protein, for example. Four days later, animals are anesthetized with ketamine and xylazine, and the trans-epithelial electric potential difference across the nasal epithelium (Vt) is measured. During measurement of Vt, the nasal mucosa is perfused at a rate of 50 µl/min with a Ringer's solution containing: 135 mM NaCl, 2.4 mM KH2PO4, 0.6 mM K2HPO4, 1.2 mM CaCl2, 1.2 mM MgCl2, and 10 mM Hepes (pH 7.4 with NaOH). Three solutions are used: (i) Ringer's solution containing 100 µM amiloride; (ii) Ringer's solution containing 135 mM Na-gluconate substituted for NaCl plus amiloride; and (iii) Na-gluconate Ringer's solution containing 10 µM isoproterenol and amiloride. Measurements are made after perfusion for 5 min.

The infected nasal epithelia are treated epithelia with amiloride to inhibit Na+ channels and then Vt is measured in response to perfusion with solutions containing a low Cl-concentration and isoproterenol to elevate cellular cAMP levels. Expression of the adenoviral vectors of the invention expressing a partially-deleted CFTR protein correct the nasal voltage defect to a similar extent as wild-type CFTR and to levels similar to those of non-CF mice. This method demonstrates the successful introduction of the adenoviral vectors of the invention, and an appropriate biosynthesis, localization, and functional activity of the transgene.

Example 7

Expression in Humans of Adenoviral-based Vectors Incorporating Truncated CMVie Enhancer-promoters Adenoviral vectors of the invention (e.g., $10^8$ particles, $10^9$ particles, $5 \times 10^9$ particles, $10^{10}$ particles) are administered to a human intranasally as Ad:CaPi coprecipitates in multiple instillations delivered several minutes apart. The adenoviral-infected nasal epithelium expresses the transgene at relatively high levels. The encoded protein appropriately is trafficked through the cell and demonstrates functional and/or therapeutic activity. In a human with CF airway disease, the expression of the transgene in the adenoviral-infected nasal epithelium ameliorates certain symptoms of the disease.

The foregoing merely illustrates the principles of the present invention. Various modifications and alterations to the described embodiments will be apparent to those of ordinary skill in the art in view of the teachings herein. It will thus be appreciated that those of ordinary skill in the art will be able to make and use the present invention in ways that, although not explicitly shown or described herein, embody the principles of the invention and are thus within the spirit and scope of the invention.

The contents of all publications and references cited herein are hereby incorporated herein by reference in their entireties

We claim:

1. An isolated nucleic acid comprising:
   a functional truncated human cytomegalovirus immediate-early enhancer-promoter region that comprises the nucleic acid sequence of SEQ ID NO:1 and that lacks the nucleotide repeat units of 16 and 21 base pairs of a full length human cytomegalovirus immediate early enhancer-promoter region.

2. The isolated nucleic acid of claim 1 operably linked to a transgene.

3. The isolated nucleic acid of claim 2, wherein the transgene comprises a nucleic acid encoding a CFTR protein having a deletion in the R domain.

4. The isolated nucleic acid of claim 3, wherein the nucleic acid encoding a CFTR protein having a deletion in the R domain has the sequence of SEQ ID NO:3.

5. A vector comprising the nucleic acid of claim 2.

6. A vector comprising the nucleic acid of claim 3.

7. A vector comprising the nucleic acid of claim 4.

8. The vector of claim 5, wherein the vector is selected from the group consisting of a plasmid, a cosmid, a phagemid, a bacteriophage, a bacterial artificial chromosome, a yeast artificial chromosome, a human artificial chromosome, a retrovirus vector, an adenovirus vector, an adeno-associated virus vector, a herpes virus vector, an Epstein-Barr virus vector, and a vaccinia virus vector.

9. The vector of claim 6, wherein the vector is selected from the group consisting of a plasmid, a cosmid, a phagemid, a bacteriophage, a bacterial artificial chromosome, a yeast artificial chromosome, a human artificial chromosome, a retrovirus vector, an adenovirus vector, an adeno-associated virus vector, a herpes virus vector, an Epstein-Barr virus vector, and a vaccinia virus vector.

10. The vector of claim 7, wherein the vector is selected from the group consisting of a plasmid, a cosmid, a phagemid, a bacteriophage, a bacterial artificial chromosome, a yeast artificial chromosome, a human artificial chromosome, a retrovirus vector, an adenovirus vector, an adeno-associated virus vector, a herpes virus vector, an Epstein-Barr virus vector, and a vaccinia virus vector.

11. The vector of claim 8, wherein the adeno-associated virus vector is an AAV5-based vector.

12. The vector of claim 9, wherein the adeno-associated virus vector is an AAV5-based vector.

13. The vector of claim 10, wherein the adeno-associated virus vector is an AAV5-based vector.

14. A cultured cell comprising the vector of claim 5.

15. A cultured cell comprising the vector of claim 6.

16. A cultured cell comprising the vector of claim 7.

* * * * *

SEQUENCE LISTING

<160> NUMBER OF SEQ ID NOS: 5

<210> SEQ ID NO 1
<211> LENGTH: 173
<212> TYPE: DNA
<213> ORGANISM: Unknown
<220> FEATURE:
<223> OTHER INFORMATION: Unable to Identify

<400> SEQUENCE: 1

```
actcacgggg atttccaagt ctccacccca ttgacgtcaa tgggagtttg ttttggcacc      60
aaaatcaacg ggactttcca aaatgtcgta ataacccgc cccgttgacg caaatgggcg     120
```

```
gtaggcgtgt acggtgggag gtctatataa gcagagctcg tttagtgaac cgt         173

<210> SEQ ID NO 2
<211> LENGTH: 113
<212> TYPE: DNA
<213> ORGANISM: Unknown
<220> FEATURE:
<223> OTHER INFORMATION: Unable to Identify

<400> SEQUENCE: 2
aaaatcaacg ggactttcca aaatgtcgta ataacccgc cccgttgacg caaatgggcg    60
gtaggcgtgt acggtgggag gtctatataa gcagagctcg tttagtgaac cgt         113

<210> SEQ ID NO 3
<211> LENGTH: 4287
<212> TYPE: DNA
<213> ORGANISM: Unknown
<220> FEATURE:
<223> OTHER INFORMATION: Unable to Identify

<400> SEQUENCE: 3
atgcagaggt cgcctctgga aaaggccagc gttgtctcca acttttttt cagctggacc    60 agaccaattt tgaggaaagg atacagacag cgcctggaat tgtcagacat ataccaaatc   120
ccttctgttg attctgctga caatctatct gaaaaattgg aaagagaatg ggatagagag   180
ctggcttcaa agaaaaatcc taaactcatt aatgccttc ggcgatgttt tttctggaga    240
tttatgttct atggaatctt tttatattta ggggaagtca ccaaagcagt acagcctctc   300
ttactgggaa gaatcatagc ttcctatgac ccggataaca aggaggaacg ctctatcgcg   360
atttatctag gcataggctt atgccttctc tttattgtga ggacactgct cctacaccca   420 gccattttg gccttcatca cattggaatg cagatgagaa tagctatgtt tagtttgatt    480
tataagaaga ctttaaagct gtcaagccgt gttctagata aataagtat tggacaactt    540 gttagtctcc tttccaacaa cctgaacaaa tttgatgaag acttgcatt ggcacatttc    600 gtgtggatcg ctcctttgca gtggcactc tccatggggc taatctggga gttgttacag    660
gcgtctgcct tctgtggact tggtttcctg atagtccttg cccttttca ggctgggcta    720 gggagaatga tgatgaagta cagagatcag agagctggga gatcagtga aagacttgtg    780 attacctcag aaatgattga aaatatccaa tctgttaagg catactgctg ggaagaagca   840
atggaaaaaa tgattgaaaa cttaagacaa acagaactga aactgactcg gaaggcagcc   900
tatgtgagat acttcaatag ctcagccttc ttcttctcag ggttctttgt ggtgttttta   960
tctgtgcttc cctatgcact aatcaaagga atcatcctcc ggaaaatatt caccaccatc   1020
tcattctgca ttgttctgcg catggcggtc actcggcaat tccctgggc tgtacaaaca   1080 tggtatgact ctcttggagc aataaacaaa atacaggatt tcttacaaaa gcaagaatat   1140
aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg gtgatgacag cctcttcttc agtaatttct cacttcttgg tactcctgtc   1320
ctgaaagata ttaatttcaa gatagaaaga ggacagttgt tggcggttgc tggatccact   1380
ggagcaggca agacttcact tctaatgatg attatgggag aactggagcc ttcagagggt   1440
aaaattaagc acagtggaag aatttcattc tgttctcagt tttcctggat tatgcctggc   1500
accattaaag aaaatatcat ctttggtgtt tcctatgatg aatatagata cagaagcgtc   1560
```

```
atcaaagcat gccaactaga agaggacatc tccaagtttg cagagaaaga caatatagtt   1620
cttggagaag gtggaatcac actgagtgga ggtcaacgag caagaatttc tttagcaaga   1680
gcagtataca aagatgctga tttgtattta ttagactctc cttttggata cctagatgtt   1740
ttaacagaaa aagaaatatt tgaaagctgt gtctgtaaac tgatggctaa caaaactagg   1800
attttggtca cttctaaaat ggaacattta aagaaagctg acaaaatatt aattttgcat   1860
gaaggtagca gctattttta tgggacattt tcagaactcc aaaatctaca gccagacttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tacgcttcag gcacgaagga ggcagtctgt cctgaacctg   2160
atgacacact cagttaacca aggtcagaac attcaccgaa agacaacagc atccacacga   2220
aaagtgtcac tgcccctca ggcaaacttg actgaactgg atatatattc aagaaggtta   2280
tctcaagaaa ctggcttgga ataagtgaa gaaattaacg aagaagactt aaaggagtgc   2340
ttttttgatg atatggagag cataccagca gtgactacat ggaacacata ccttcgatat   2400
attactgtcc acaagagctt aattttttgtg ctaatttggt gcttagtaat ttttctggca   2460
gaggtggctg cttctttggt tgtgctgtgg ctccttggaa acactcctct tcaagacaaa   2520
gggaatagta ctcatagtag aaataacagc tatgcagtga ttatcaccag caccagttcg   2580
tattatgtgt tttacattta cgtgggagta gccgacactt tgcttgctat gggattcttc   2640
agaggtctac cactggtgca tactctaatc acagtgtcga aaattttaca ccacaaaatg   2700
ttacattctg ttcttcaagc acctatgtca accctcaaca cgttgaaagc aggtgggatt   2760
cttaatagat tctccaaaga tatagcaatt ttggatgacc ttctgcctct taccatattt   2820
gacttcatcc agttgttatt aattgtgatt ggagctatag cagttgtcgc agttttacaa   2880
ccctacatct ttgttgcaac agtgccagtg atagtggctt ttattatgtt gagagcatat   2940
ttcctccaaa cctcacagca actcaaacaa ctggaatctg aaggcaggag tccaatttc   3000 actcatcttg ttacaagctt aaaaggacta tggacacttc gtgccttcgg acggcagcct   3060
tactttgaaa ctctgttcca caaagctctg aatttacata ctgccaactg gttcttgtac   3120
ctgtcaacac tgcgctggtt ccaaatgaga atagaaatga tttttgtcat cttcttcatt   3180
gctgttacct tcatttccat tttaacaaca ggagaaggag aaggaagagt tggtattatc   3240
ctgactttag ccatgaatat catgagtaca ttgcagtggg ctgtaaactc cagcatagat   3300
gtggatagct tgatgcgatc tgtgagccga gtctttaagt tcattgacat gccaacagaa   3360
ggtaaaccta ccaagtcaac caaaccatac aagaatggcc aactctcgaa agttatgatt   3420
attgagaatt cacacgtgaa gaaagatgac atctggccct caggggccaa atgactgtc   3480 aaagatctca cagcaaaata cacagaaggt ggaaatgcca tattagagaa catttccttc   3540
tcaataagtc ctggccagag ggtgggcctc ttgggaagaa ctggatcagg gaagagtact   3600
ttgttatcag cttttttgag actactgaac actgaaggaa aaatccagat cgatggtgtg   3660
tcttgggatt caataacttt gcaacagtgg aggaaagcct tggagtgat accacagaaa   3720 gtatttattt tttctggaac atttagaaaa aacttggatc cctatgaaca gtggagtgat   3780
caagaaatat ggaaagttgc agatgaggtt gggctcagat ctgtgataga acagtttcct   3840
gggaagcttg actttgtcct tgtggatggg ggctgtgtcc taagccatgg ccacaagcag   3900
ttgatgtgct tggctagatc tgttctcagt aaggcgaaga tcttgctgct tgatgaaccc   3960
```

```
agtgctcatt tggatccagt aacataccaa ataattagaa gaactctaaa acaagcattt    4020
gctgattgca cagtaattct ctgtgaacac aggatagaag caatgctgga atgccaacaa    4080 ttttttggtca tagaagagaa caaagtgcgg cagtacgatt ccatccagaa actgctgaac    4140
gagaggagcc tcttccggca agccatcagc ccctccgaca gggtgaagct ctttccccac    4200
cggaactcaa gcaagtgcaa gtctaagccc cagattgctg ctctgaaaga ggagacagaa    4260
gaagaggtgc aagatacaag gctttag                                        4287
```

<210> SEQ ID NO 4
<211> LENGTH: 4576
<212> TYPE: DNA
<213> ORGANISM: Unknown
<220> FEATURE:
<223> OTHER INFORMATION: Unable to Identify

<400> SEQUENCE: 4

```
gcggccgcac tcacggggat ttccaagtct ccaccccatt gacgtcaatg ggagtttgtt      60
ttggcaccaa atcaacggg acttttccaaa atgtcgtaat aaccccgccc cgttgacgca    120
aatgggcggt aggcgtgtac ggtgggaggt ctatataagc agagctcgtt tagtgaaccg    180
tcagaattct cgagtgatcg aaagagcctg ctaaagcaaa aaagaagtca ccatgcagag    240
gtcgcctctg gaaaaggcca gcgttgtctc caaactttt ttcagctgga ccagaccaat     300
tttgaggaaa ggatacagac agcgcctgga attgtcagac atataccaaa tcccttctgt    360
tgattctgct gacaatctat ctgaaaaatt ggaaagagaa tgggatagag agctggcttc    420
aaagaaaaat cctaaactca ttaatgccct tcggcgatgt tttttctgga gatttatgtt    480
ctatggaatc ttttttatatt taggggaagt caccaaagca gtacagcctc tcttactggg    540
aagaatcata gcttcctatg acccggataa caaggaggaa cgctctatcg cgatttatct    600
aggcataggc ttatgccttc tctttattgt gaggacactg ctcctacacc cagccatttt    660
tggccttcat cacattggaa tgcagatgag aatagctatg tttagtttga tttataagaa    720
gactttaaag ctgtcaagcc gtgttctaga taaaataagt attggacaac ttgttagtct    780
cctttccaac aacctgaaca aatttgatga aggacttgca ttggcacatt tcgtgtggat    840
cgctcctttg caagtggcac tcctcatggg gctaatctgg gagttgttac aggcgtctgc    900
cttctgtgga cttggttttcc tgatagtcct tgccctttt caggctgggc tagggagaat    960
gatgatgaag tacagagatc agagagctgg gaagatcagt gaaagacttg tgattacctc   1020
agaaatgatt gaaaatatcc aatctgttaa ggcatactgc tgggaagaag caatggaaaa   1080
aatgattgaa aacttaagac aaacagaact gaaactgact cggaaggcag cctatgtgag   1140
atacttcaat agctcagcct tcttcttctc agggttcttt gtggtgtttt atctgtgct    1200 tcccctatgca ctaatcaaag gaatcatcct ccggaaaata ttcaccacca tctcattctg   1260
cattgttctg cgcatggcgg tcactcggca atttcctgg gctgtacaaa catggtatga    1320
ctctcttgga gcaataaaca aaatacagga tttcttacaa aagcaagaat ataagacatt   1380
ggaatataac ttaacgacta cagaagtagt gatggagaat gtaacagcct ctgggaggga   1440
gggatttggg gaattatttg agaaagcaaa acaaaacaat aacaatagaa aaacttctaa   1500
tggtgatgac agcctcttct tcagtaattt ctcacttctt ggtactcctg tcctgaaaga   1560
tattaatttc aagatagaaa gaggacagtt gttggcggtt gctggatcca ctggagcagg   1620
caagacttca cttctaatga tgattatggg agaactggag ccttcagagg gtaaaattaa   1680
```

```
gcacagtgga agaatttcat tctgttctca gttttcctgg attatgcctg gcaccattaa    1740
agaaaatatc atctttggtg tttcctatga tgaatataga tacagaagcg tcatcaaagc    1800
atgccaacta agaggaca ctccaagtt tgcagagaaa gacaatatag ttcttggaga       1860
aggtggaatc acactgagtg gaggtcaacg agcaagaatt tctttagcaa gagcagtata    1920
caaagatgct gatttgtatt tattagactc tccttttgga tacctagatg tttttaacaga   1980 aaaagaaata tttgaaagct gtgtctgtaa actgatggct aacaaaacta ggattttggt    2040
cacttctaaa atggaacatt taaagaaagc tgacaaaata ttaattttgc atgaaggtag    2100
cagctatttt tatgggacat tttcagaact ccaaaatcta cagccagact ttagctcaaa    2160
actcatggga tgtgattctt tcgaccaatt tagtgcagaa agaagaaatt caatcctaac    2220
tgagacctta caccgtttct cattagaagg agatgctcct gtctcctgga cagaaacaaa    2280
aaaacaatct tttaaacaga ctggagagtt tggggaaaaa aggaagaatt ctattctcaa    2340
tccaatcaac tctacgcttc aggcacgaag gaggcagtct gtcctgaacc tgatgacaca   2400
ctcagttaac caaggtcaga acattcaccg aaagacaaca gcatccacac gaaaagtgtc    2460 actgcccct caggcaaact tgactgaact ggatatatat tcaagaaggt tatctcaaga     2520
aactggcttg gaaataagtg aagaaattaa cgaagaagac ttaaaggagt gcttttttga    2580
tgatatggag agcataccag cagtgactac atggaacaca taccttcgat atattactgt    2640
ccacaagagc ttaattttg tgctaatttg gtgcttagta atttttctgg cagaggtggc     2700
tgcttctttg gttgtgctgt ggctccttgg aaacactcct cttcaagaca agggaatag     2760 tactcatagt agaaataaca gctatgcagt gattatcacc agcaccagtt cgtattatgt    2820
gttttacatt tacgtgggag tagccgacac tttgcttgct atgggattct tcagaggtct    2880
accactggtg catactctaa tcacagtgtc gaaaattta caccacaaaa tgttacattc      2940
tgttcttcaa gcacctatgt caaccctcaa cacgttgaaa gcaggtggga ttcttaatag     3000
attctccaaa gatatagcaa ttttggatga ccttctgcct cttaccatat ttgacttcat    3060
ccagttgtta ttaattgtga ttggagctat agcagttgtc gcagttttac aaccctacat    3120
ctttgttgca acagtgccag tgatagtggc ttttattatg ttgagagcat atttcctcca    3180
aacctcacag caactcaaac aactggaatc tgaaggcagg agtccaattt tcactcatct    3240
tgttacaagc ttaaaaggac tatggacact tcgtgccttc ggacggcagc cttactttga    3300
aactctgttc cacaaagctc tgaatttaca tactgccaac tggttcttgt acctgtcaac    3360
actgcgctgg ttccaaatga aatagaaat gattttgtc atcttcttca ttgctgttac     3420
cttcatttcc attttaacaa caggagaagg agaaggaaga gttggtatta tcctgacttt    3480
agccatgaat atcatgagta cattgcagtg ggctgtaaac tccagcatag atgtggatag    3540
cttgatgcga tctgtgagcc gagtctttaa gttcattgac atgccaacag aaggtaaacc    3600
taccaagtca accaaaccat acaagaatgg ccaactctcg aaagttatga ttattgagaa    3660
ttcacacgtg aagaaagatg acatctggcc ctcaggggc caaatgactg tcaaagatct    3720
cacagcaaaa tacacagaag gtggaaatgc catattagaa acatttcct tctcaataag     3780 tcctggccag agggtgggcc tcttgggaag aactggatca gggaagagta ctttgttatc    3840
agcttttttg agactactga acactgaagg agaaatccag atcgatggtg tgtcttggga    3900
ttcaataact ttgcaacagt ggaggaaagc ctttggagtg ataccacaga agtatttat     3960 tttttctgga acatttagaa aaaacttgga tcccctatgaa cagtggagtg atcaagaaat   4020
atggaaagtt gcagatgagg ttgggctcag atctgtgata gaacagtttc ctgggaagct   4080
```

```
tgactttgtc cttgtggatg ggggctgtgt cctaagccat ggccacaagc agttgatgtg    4140
cttggctaga tctgttctca gtaaggcgaa gatcttgctg cttgatgaac ccagtgctca    4200
tttggatcca gtaacatacc aaataattag aagaactcta aaacaagcat ttgctgattg    4260
cacagtaatt ctctgtgaac acaggataga agcaatgctg aatgccaac aattttttggt    4320 catagaagag aacaaagtgc ggcagtacga ttccatccag aaactgctga acgagaggag    4380
cctcttccgg caagccatca gcccctccga cagggtgaag ctctttcccc accggaactc    4440
aagcaagtgc aagtctaagc cccagattgc tgctctgaaa gaggagacag aagaaggt     4500 gcaagataca aggctttaga ataaaacatc tttattttca ttacatctgt gtgttggttt    4560
tttgtgtggc ggccgc                                                    4576

<210> SEQ ID NO 5
<211> LENGTH: 4516
<212> TYPE: DNA
<213> ORGANISM: Unknown
<220> FEATURE:
<223> OTHER INFORMATION: Unable to Identify

<400> SEQUENCE: 5
gcggccgcaa aatcaacggg actttccaaa atgtcgtaat aaccccgccc cgttgacgca      60
aatgggcggt aggcgtgtac ggtgggaggt ctatataagc agagctcgtt tagtgaaccg     120
tcagaattct cgagtgatcg aaagagcctg ctaaagcaaa aaagaagtca ccatgcagag     180
gtcgcctctg gaaaaggcca gcgttgtctc caaacttttt ttcagctgga ccagaccaat     240
tttgaggaaa ggatacagac agcgcctgga attgtcagac atataccaaa tcccttctgt     300
tgattctgct gacaatctat ctgaaaaatt ggaaagagaa tgggatagag agctggcttc     360
aaagaaaaat cctaaactca ttaatgccct tcggcgatgt ttttttctgga gatttatgtt    420 ctatggaatc ttttttatatt tagggggaagt caccaaagca gtacagcctc tcttactggg    480
aagaatcata gcttcctatg acccggataa caaggaggaa cgctctatcg cgatttatct     540
aggcataggc ttatgccttc tctttattgt gaggacactg ctcctacacc cagccatttt    600
tggccttcat cacattggaa tgcagatgag aatagctatg tttagtttga tttataagaa     660
gactttaaag ctgtcaagcc gtgttctaga taaaataagt attggacaac ttgttagtct     720
cctttccaac aacctgaaca aatttgatga aggacttgca ttggcacatt tcgtgtggat     780
cgctcctttg caagtggcac tcctcatggg gctaatctgg gagttgttac aggcgtctgc     840
cttctgtgga cttggttttcc tgatagtcct tgcccttttt caggctgggc tagggagaat    900
gatgatgaag tacagagatc agagagctgg gaagatcagt gaaagacttg tgattacctc     960
agaaatgatt gaaaatatcc aatctgttaa ggcatactgc tgggaagaag caatggaaaa    1020
aatgattgaa aacttaagac aaacagaact gaaactgact cggaaggcag cctatgtgag    1080
atacttcaat agctcagcct tcttcttctc agggttcttt gtggtgtttt atctgtgct     1140 tcccctatgca ctaatcaaag gaatcatcct ccggaaaata ttcaccacca tctcattctg    1200
cattgttctg cgcatggcgg tcactcggca atttccctgg gctgtacaaa catggtatga    1260
ctctcttgga gcaataaaca aaatacagga tttcttacaa agcaagaat ataagacatt     1320 ggaatataac ttaacgacta cagaagtagt gatggagaat gtaacagcct tctgggagga    1380
gggatttggg gaattatttg agaaagcaaa acaaaacaat aacaatagaa aaacttctaa    1440
tggtgatgac agcctcttct tcagtaattt ctcacttctt ggtactcctg tcctgaaaga    1500
```

```
tattaatttc aagatagaaa gaggacagtt gttggcggtt gctggatcca ctggagcagg    1560
caagacttca cttctaatga tgattatggg agaactggag ccttcagagg gtaaaattaa    1620
gcacagtgga agaatttcat tctgttctca gttttcctgg attatgcctg caccattaa     1680 agaaaatatc atctttggtg tttcctatga tgaatataga tacagaagcg tcatcaaagc    1740
atgccaacta agaggacta  ctccaagtt tgcagagaaa gacaatatag ttcttggaga     1800
aggtggaatc acactgagtg gaggtcaacg agcaagaatt tctttagcaa gagcagtata    1860
caaagatgct gatttgtatt tattagactc tccttttgga tacctagatg ttttaacaga    1920
aaaagaaata tttgaaagct gtgtctgtaa actgatgggc aacaaaacta ggattttggt    1980
cacttctaaa atggaacatt taaagaaagc tgacaaaata ttaattttgc atgaaggtag    2040
cagctatttt tatgggacat tttcagaact ccaaaatcta cagccagact ttagctcaaa    2100
actcatggga tgtgattctt tcgaccaatt tagtgcagaa agaagaaatt caatcctaac    2160 tgagaccta  caccgtttct cattagaagg agatgctcct gtctcctgga cagaaacaaa    2220
aaaacaatct tttaaacaga ctggagagtt tggggaaaaa aggaagaatt ctattctcaa    2280
tccaatcaac tctacgcttc aggcacgaag gaggcagtct gtcctgaacc tgatgacaca    2340
ctcagttaac caaggtcaga acattcaccg aaagacaaca gcatccacac gaaaagtgtc    2400
actgccccct caggcaaact tgactgaact ggatatatat tcaagaaggt tatctcaaga    2460
aactggcttg gaaataagtg aagaaattaa cgaagaagac ttaaaggagt gcttttttga    2520
tgatatggag agcataccag cagtgactac atggaacaca taccttcgat atattactgt    2580
ccacaagagc ttaattttg  tgctaatttg gtgcttagta atttttctgg cagaggtggc    2640
tgcttctttg gttgtgctgt ggctccttgg aaacactcct cttcaagaca aagggaatag    2700
tactcatagt agaaataaca gctatgcagt gattatcacc agcaccagtt cgtattatgt    2760
gttttacatt tacgtgggag tagccgacac tttgcttgct atgggattct tcagaggtct    2820
accactggtg catactctaa tcacagtgtc gaaaatttta caccacaaaa tgttacattc    2880
tgttcttcaa gcacctatgt caaccctcaa cacgttgaaa gcaggtggga ttcttaatag    2940
attctccaaa gatatagcaa ttttggatga ccttctgcct cttaccatat ttgacttcat    3000
ccagttgtta ttaattgtga ttggagctat agcagttgtc gcagttttac aaccctacat    3060
ctttgttgca acagtgccag tgatagtggc ttttattatg ttgagagcat atttcctcca    3120
aacctcacag caactcaaac aactggaatc tgaaggcagg agtccaattt tcactcatct    3180
tgttacaagc ttaaaggac  tatggacact tcgtgccttc ggacggcagc cttactttga    3240
aactctgttc cacaaagctc tgaatttaca tactgccaac tggttcttgt acctgtcaac    3300
actgcgctgg ttccaaatga aatagaaat  gattttgtc  atcttcttca ttgctgttac    3360
cttcatttcc attttaacaa caggagaagg agaaggaaga gttggtatta tcctgacttt    3420
agccatgaat atcatgagta cattgcagtg ggctgtaaac tccagcatag atgtggatag    3480
cttgatgcga tctgtgagcc gagtctttaa gttcattgac atgccaacag aaggtaaacc    3540
taccaagtca accaaaccat acaagaatgg ccaactctcg aaagttatga ttattgagaa    3600
ttcacacgtg aagaaagatg acatctggcc ctcaggggc  caaatgactg tcaaagatct    3660
cacagcaaaa tacacagaag gtggaaatgc catattagag aacatttcct tctcaataag    3720
tcctggccag agggtgggcc tcttgggaag aactggatca gggaagagta ctttgttatc    3780
agcttttttg agactactga acactgaagg agaaatccag atcgatgtgt gtcttggga     3840 ttcaataact ttgcaacagt ggaggaaagc ctttggagtg ataccacaga aagtatttat    3900
```

```
ttttctgga acatttagaa aaaacttgga tccctatgaa cagtggagtg atcaagaaat    3960
atggaaagtt gcagatgagg ttgggctcag atctgtgata gaacagtttc ctgggaagct    4020
tgactttgtc cttgtggatg ggggctgtgt cctaagccat ggccacaagc agttgatgtg    4080
cttggctaga tctgttctca gtaaggcgaa gatcttgctg cttgatgaac ccagtgctca    4140
tttggatcca gtaacatacc aaataattag aagaactcta aaacaagcat ttgctgattg    4200
cacagtaatt ctctgtgaac acaggataga agcaatgctg gaatgccaac aatttttggt    4260
catagaagag aacaaagtgc ggcagtacga ttccatccag aaactgctga acgagaggag    4320
cctcttccgg caagccatca gcccctccga cagggtgaag ctctttcccc accggaactc    4380
aagcaagtgc aagtctaagc cccagattgc tgctctgaaa gaggagacag aagaagaggt    4440
gcaagataca aggctttaga ataaaacatc tttattttca ttacatctgt gtgttggttt    4500
tttgtgtggc ggccgc                                                   4516
```